United States Patent [19]

Uchikawa et al.

[11] Patent Number: 5,589,936

[45] Date of Patent: Dec. 31, 1996

[54] OPTICAL MEASURING APPARATUS FOR MEASURING PHYSICHEMICAL PROPERTIES

[75] Inventors: Kiyoshi Uchikawa, Tokyo; Takayuki Suga; Akira Furusawa, both of Tsukuba, all of Japan

[73] Assignee: Nikon Corporation, Tokyo, Japan

[21] Appl. No.: 120,874

[22] Filed: Sep. 10, 1993

[30] Foreign Application Priority Data

Sep. 14, 1992 [JP] Japan ................................. 4-244637
Oct. 22, 1992 [JP] Japan ................................. 4-284701
May 26, 1993 [JP] Japan ................................. 5-123778
May 26, 1993 [JP] Japan ................................. 5-123779

[51] Int. Cl.$^6$ ............................................... G01B 9/02
[52] U.S. Cl. ............................................... 356/345; 356/359
[58] Field of Search ................................. 356/357, 355, 356/359, 381, 360, 345; 382/8

[56] References Cited

U.S. PATENT DOCUMENTS 5,133,601   7/1992   Cohen et al. ........................... 356/359

FOREIGN PATENT DOCUMENTS 2-252123A   10/1990   Japan .
3-137828A    6/1991   Japan .
3-141100A    6/1991   Japan .
3-183033A    8/1991   Japan .

OTHER PUBLICATIONS

Optics Letters, vol. 16, No. 1, Jan. 1991, pp. 10–12, "Phase Modulation Technique For Accumulated Photon Echo' Whole Document" by Saikan et al.
Optics Letters, vol. 16, No. 1, Jan. 1991, pp. 13–14, "Fluorescence Detection Of Femtosecond Accumulated Photon Echo' Whole Document" by Uchikawa et al.
Physical Review B, vol. 45, No. 22, Jun. 1, 1992, pp. 12752–12759, "Stimulated Photon Echo Spectroscopy" by Yano et al.
Journal of the Optical Society of America B, vol. B9, No. 6, Jun. 1992, pp. 941–945, "Ultrafast Dephasing of Resorufin, etc.", by Gruzdev et al.
Journal of the Optical Society of America B, vol. B9, No. 6, Jun. 1992, pp. 987–991, "Spectral Hole Burning,etc.", by Bernet et al.
Applied Spectroscopy, vol. 45, No. 6, Jul. 1991, pp. 1041–1045, "Three Dimensional Space and Time Resolved Fluorescence Spectroscopy", by Sasaki et al.
Optics Letters, vol. 16, No. 21, Nov. 1991, pp. 1683–1685, "Femtosecond Time Resolved Interferometry" by Minoshima et al.

*Primary Examiner*—Samuel A. Turner
*Attorney, Agent, or Firm*—Pennie & Edmonds

[57] ABSTRACT

The present invention relates to an optical measuring apparatus for measuring physicochemical properties of specimen, utilizing the optical echo which is a nonlinear optical phenomenon. Light emitted from a laser beam source in the optical measuring apparatus of the present invention is split into two beams, one of which is optically delayed by an optical delay unit and the other of which is phase-modulated at a predetermined frequency by a phase modulator. An optical mixer mixes the two beams outgoing from the optical delay unit and from the phase modulator, and the mixed beam is guided onto a specimen to form a light spot thereon. Light from the specimen is detected by a photodetector, and a modulation component even times larger than the modulation frequency of phase modulator is extracted from the output signal from the photodetector. The physicochemical properties of specimen can be measured by detecting an intensity of optical echo depending upon the optical delay time set by the optical delay unit.

16 Claims, 18 Drawing Sheets

OPTICAL MEASURING APPARATUS FOR MEASURING PHYSICHEMICAL PROPERTIES

BACKGROUND OF THE INVENTION

1. Field of the Invention

The present invention relates to an optical measuring apparatus for measuring physicochemical properties of specimen utilizing the optical echo which is a nonlinear optical phenomenon.

2. Related Background Art

There are various laser scanning microscopes with laser beam source conventionally known as the technology for measuring a specimen in high definition. As a typical example, a confocal laser scanning microscope has the structure for measurement in which a spot beam is guided to irradiate a specimen located at a focal position of illumination system and in which light from the specimen is focused on a pin hole then to be detected by a photo detector. Since the depth of focus is very shallow for image obtained in measurement by the confocal laser scanning microscope, the microscope has a superior advantage that an infinite depth of focus can be obtained by so-called sectioning effect in scanning in the direction of optical axis.

Meanwhile, there is no great qualitative difference made between information of specimen obtained in measurement with conventional laser scanning microscopes represented by such a confocal laser scanning microscope and information obtained from image through conventional optical microscopes using no laser beam source as more generally known. In other words, it can be said that no technical (qualitative) great difference exists in measuring structural or configurational characteristics of specimen between the laser scanning microscopes and the more general optical microscopes using no laser light. Further, the laser scanning microscopes have no function to measure the general properties of specimen including not only the external properties such as the structure and the configuration but also the physicochemical properties such as microscopic dynamics (in other words, inherent properties).

It is, however, very important for example in medical field to measure the physicochemical properties of specimen such in addition to the external properties of specimen extirpated from organism. The conventional laser scanning microscopes were not provided with such a function to meet the demand. The demand is not only in medical field but also in other diverse fields, for measuring apparatus which permit the measurement of physicochemical properties of specimen.

SUMMARY OF THE INVENTION

The present invention has been accomplished taking the circumstances as described above into consideration.

It is a first object of the present invention to provide an optical measuring apparatus which can measure the physicochemical properties of specimen.

It is a second object of the present invention to provide an optical measuring apparatus which can measure the physicochemical properties of specimen and which can also measure the properties such as the structure and the configuration of specimen.

It is a third object of the present invention to provide a compact and simple optical measuring apparatus having the structure applicable to the conventional optical microscopes.

It is a fourth object of the present invention to provide an optical measuring apparatus which realizes measurement at high SN ratio (measurement with less noise components to real measuring signal).

Further, it is a fifth object of the present invention to provide an optical measuring apparatus which permits measurement not only in a small range in specimen but also in a large area therein.

The present invention will be described in detail hereinafter with preferred embodiments. The fundamental technical idea of the present invention including the embodiments is to measure the physicochemical properties of specimen by irradiating a specimen with certain pulse light and observing the optical echo phenomenon caused thereby.

In optics, the optically pumped state of substance, for example a specimen, is expressed by equation of motion of density matrix (Liouville equation). For convenience sake, a relaxation time of diagonal elements of density matrix is called as longitudinal relaxation time ($T_1$ time) while a relaxation time of off-diagonal elements as transverse relaxation time ($T_2$ time), which are so discriminated from each other. It is considered that the longitudinal relaxation means a process of relaxation of optically pumped state with energy emission and that the transverse relaxation means a process in which the coherency of mixing of quantum states caused in substance by incident light is being disturbed.

The phenomenon of optical echo (as also referred to as photon echo) is considered as a kind of third-order nonlinear optical effect. From among the optical echo phenomena, accumulated photon echo is described herein referring to FIG. 1. Let us assume that a substance is excited by pulse light which is resonant to the absorption band of the substance. Pulse light $E_1$ first irradiates the substance at time $t_1$. Further, pulse light $E_2$ then irradiates the substance at time $t_2$ after time $\tau$. Next, pulse light $E_3$ irradiates the substance at time $t_3$. Then, light hv is conversely radiated from the substance at time $t_4$ ($=t_3+t_2-t_1=t_3+\tau$). Such a phenomenon is the stimulated photon echo, and the light hv is stimulated photon echo light. The stimulated photon echo is characteristic in that the intensity thereof is damped in proportion to the exponential function, $\exp(-4\tau/T_2)$, at $(t_3-t_2)$ is constant.

The optical excitation by said pulse lights $E_1$, $E_2$, $E_3$ is repeated several times within the optical absorption recovery time of the substance, so that the intensity of stimulated photon echo is increased. The photon echo observed at this time is the accumulated photon echo. FIG. 1 shows that the optical excitation is repeated by pulse lights $E_1"$, $E_2"$, $E_3"$. If the optical absorption recovery time of the substance is long, the stimulated photon echo can be enhanced as the same excitation process is repeated plural times. Generally, time relation is set at either $(t_1"-t_4)\gg(t_2-t_1)$ or $(t_1"t_4)\gg(t_3-t_2)$.

The optical measuring apparatus of the present invention has been achieved paying attention to such a phenomenon. The apparatus measures the physicochemical properties of substance as specimen such that pulse light is irradiented to the substance while changing the delay time $\tau$ and that the intensity of accumulated photon echo light hv is consecutively measured to obtain the transverse relaxation time ($T_2$ time). In other words, since the transverse relaxation time changes according to the type of substance or to the state of substance, the optical measuring apparatus of the present invention perform the measurement of physicochemical properties of substance by measuring the transverse relaxation time specific to the substance.

The photon echo is a third-order nonlinear optical phenomenon, and the intensity of photon echo is lower by several figures than the intensities of excitation pulse lights $E_1$, $E_2$, $E_3$. Then, the present invention employs novel means for measuring the weak photon echo hv at high sensitivity. In more detail, pulse light $E_4$ which has the same phase property as the pulse light $E_3$ is made to interfere with photon echo hv in order to amplify changes in intensity.

The pulse light $E_4$ is generally called a probe light. In the present invention, arrival time $t_4$ of the probe light $E_4$ is changed oscillatory, for example, within the range of time $\pm \Delta \tau$, centering time of photon echo hv appeared $(t_3+t_2-t_1= t_3+\tau)$, to make the photon echo hv interfere with the probe light $E_4$. Then, the time $t_4$ described above is changed to make a full use of the interference effect. Further, when a next probe light $E_4'$ is arrived, in similar way, it is made to interfere with a next photo echo hv, and as the probe lights $E_4$, $E_4'$, $E_4''$ . . . are subsequently arrived, in similar way, every probe light is made to interfere with photon echo hv one after another.

Since subsequently appeared photon echo hv, in principle, has the same phase property as the excitation pulse lights $E_3$, $E_3'$, $E_3''$ . . . , these photon echoes hv strongly interfere with the probe lights $E_4$, $E_4'$, $E_4''$. . . . Explaining with the excitation pulse light $E_3$, if the arrival time $t_4$ of the probe light $E_4$ is weakly oscillated at the frequency f set in advance centering time of photon echo appeared $(t_3+\tau)$, phase modulation is performed, and then with the interference effect, the intensity of synthetic light between photon echo h and probe light $E_4$ is changed in synchronism therewith. The amount of changes is proportional to multiplication of electric field amplitude of photon echo hv and electric field amplitude of probe light $E_4$. If the intensity of probe light $E_4$ is stable, the amount of changes in synthetic light caused by the interference described above is proportional to changes in amplitude of photon echo hv.

The photon echo hv is appeared such that the excitation pulse lights $E_1$, $E_2$, $E_3$ resonate with the absorption state of the substance. Accordingly, the photon echo hv can theoretically be explained with imaginary part of third-order nonlinear susceptibity $\chi_{(3)}$. If the probe light $E_4$ is oscillated to phase-modulate within the range of frequency f and time$\pm\Delta\tau$ centering time of the photon echo hv appeared $(t_3+v)$, changes in intensity caused by the interference between photon echo hv and probe light $E_4$ do not appear at frequency f, but they appear at frequency of 2f, 4 f, . . . nf (n is even number). Further, when the probe lights $E_4''$, $E_4''$ . . . are arrived, in similar way, changes in intensity caused by interference appear at frequency of 2f, 4f . . . . The interference effect between photon echo hv and probe light $E_4$ appears not only in the synthetic light but also in quantum state of substance. In this case, intensity of fluorescence emitted from the substance is modulated with the even times n of modulating frequency f.

The present invention has achieved such a interference with optical system. The invention is to measure photon echo with high sensitivity by detecting synthetic light, fluorescence or light mixed with the fluorescence and the synthetic light caused by the interference with the light detecting unit and based on detected signal, amplifying changes in intensity only synchronized with frequency 2f.

In the case as shown in FIG. 1, in general, phase modulation described above is hardly achieved by fixing every period of time $(t_2-t_1)$, $(t_2''-t_1'')$ . . . at time $\tau$ and oscillating every period of time $(t_4-t_3)$, $(t_4''-t_3'')$. . . . In other words, optical system with extremely high mechanical accuracy is required.

However, the present invention has solved the problems paying attention to the physical property of the accumulated photon echo. This means that for the accumulated photon echo, the photon echo hv appears at time $(t_3+\tau)$ with no effect of phase modulation. In more detail, the photon echo hv appears at time $(t_3+t_2-t_1 =t_3+\tau)$ even though arrival time $t_2$ of excitation pulse light $E_2$ is modulated (this means that the modulation can be expressed as $t_2+\Delta\tau\cdot\sin\pi ft$ ). Accordingly, even if excitation pulses $E_2$, $E_2''$ . . . are phase-modulated similarly to the phase-modulation of probe pulse $E_4$, $E_4''$, etc. photon echo hv can be detected at high precision, similar to the way of detecting photon echo hv by using the interference effect between the photon echo hv and the probe light $E_4$.

Thus, paying attention to the property of accumulated photon echo, the present invention has accomplished an optical measuring apparatus which performs detecting at high precision even with simple structure.

In order to obtain the phase relaxation time $T_2$, in FIG. 1, said $\Delta\tau$ and f are held at stable and the amount of changes in intensity modulation component appeared at frequency 2f of synthetic light, fluorescence and their mixed light caused by changing $\tau$ is measured.

DESCRIPTION OF THE PREFERRED EMBODIMENTS

The embodiments according to the present invention will be described in detail in order.
Embodiment 1

Figure 1:
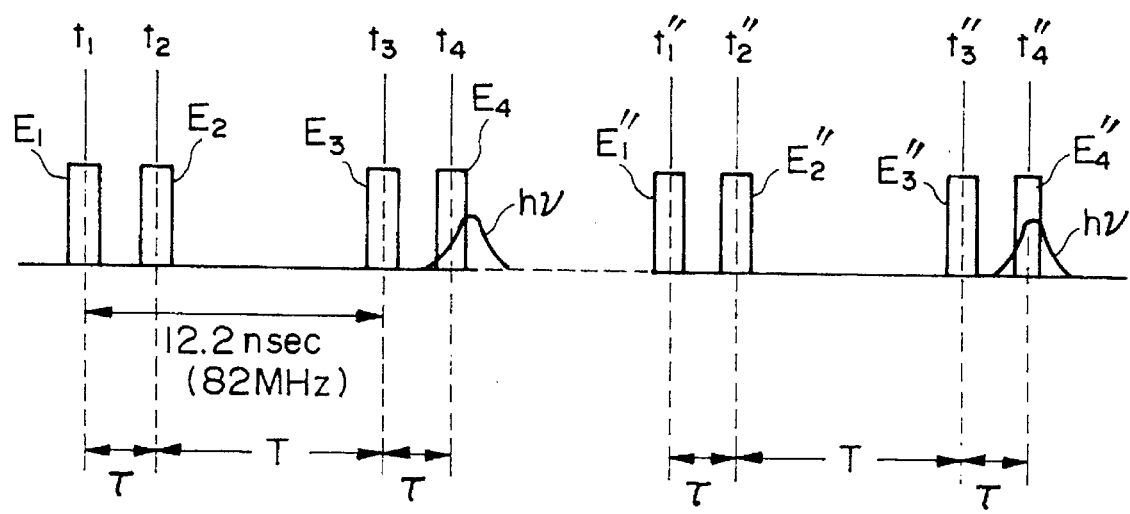
FIG. 1 is a principle explanation drawing to illustrate the principle of the present invention.
Figure 2:
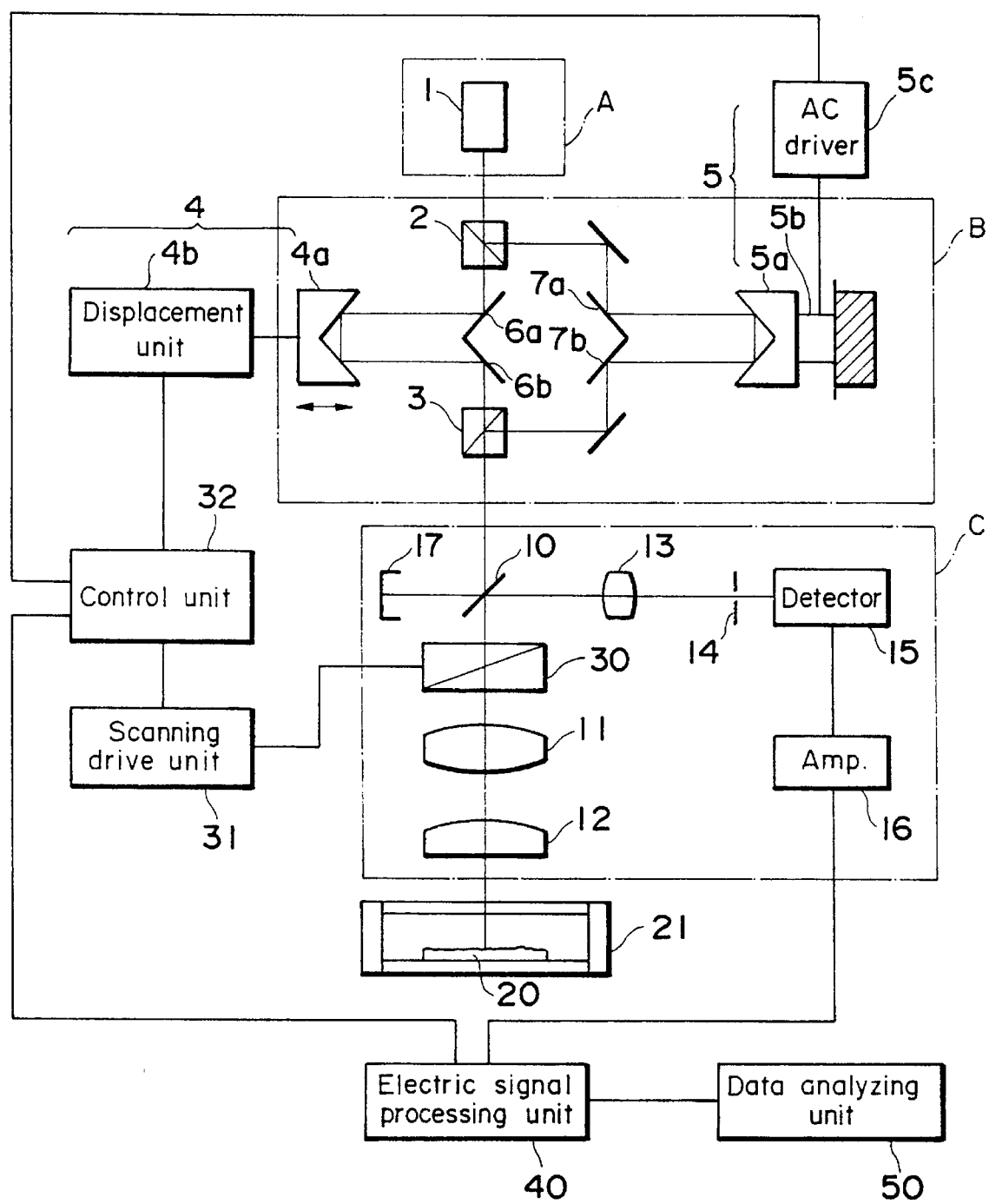
FIG. 2 is an explanatory drawing to show the structure of the first embodiment.

The first embodiment is described with FIG. 2. This embodiment relates to an optical measuring apparatus for measuring the physicochemical properties of specimen (substance).

The structure of the apparatus is briefly described first. A suitable light source has a spatial coherence with which the light source can be assumed as a point source of light on image plane and a time coherence shorter than an optical phase relaxation time of a light absorbing band to be watched in specimen. An optical system including a light splitter for splitting light from the light source into two beams and an optical mixer for mixing the two beams is preferably a 2-path interferometer such as the Michelson interferometer and the Mach-Zehnder interferometer. A delay unit has a function to change the length of one of the optical paths in the interferometer and an optical modulator has a function to phase-modulate at fixed frequency f the beam passing through the other path in the interferometer. Light outgoing from the interferometer is converged by an irradiation optical system onto or into a specimen to form a light spot. A condenser optical system guides scattered, transmitted or radiated light from the specimen onto a photodetector, and signal processing means has a function to selectively detect and amplify only an alternate current component with frequency equal to two times or arbitrary even times of the modulation frequency of the phase out of an output signal from the photodetector.

The structure is further described referring to FIG. 2. The apparatus is provided with three optical systems encircled by dotted line, that is, light source means (A), light modulation optical system (B) and confocal laser scanning optical system (C). In the present embodiment the light source means (A) has a light source 1 composed of an 80 MHz mode-locked argon laser pumped dye laser. Other lasers may be employed as light source 1, for example the multi-mode semiconductor lasers, the mode-locked semiconductor lasers, LEDs or the solid lasers.

The light splitter 2 for splitting the beam from laser beam source into two beams and the mixer 3 for mixing two split beams are polarization beam splitters. They may be replaced by semitransparent mirrors having little or no polarization property. A corner cube 4a fixed on a movable stage not shown is disposed in transmission light path of the light splitter 2, which constitutes light delay means 4 including a displacement unit 4b for displacing the movable stage. The displacement unit 4b is arranged to move the corner cube 4a as to produce a certain amount of optical delay. Phase modulation means 5 is disposed in reflection light path of the light splitter 2. An electrooptic crystal is often used generally as phase modulation means 5, but the present embodiment employs a piezoelectric device 5b fixed at one end and fixed to a corner cube 5a at the other end. An AC drive source 5c applies an AC voltage of predetermined frequency f to the piezoelectric device 5b, constituting the phase modulation means 5 of frequency f. The light splitter 2, the mixer 3, the optical delay means 4 and the phase modulation means 5 constitute the light modulation optical system (B). Orthogonal reflection planes 6a, 6b or 7a, 7b placed in the split beams are reflective surfaces for bending optical paths to guide light to the optical delay means 4 or to the phase modulation means 5, respectively, and to facilitate the optical mixing in the mixer 3. Although the optical delay means 4 is disposed in the transmission light path of light splitter 2 and the phase modulation means 5 in the reflection light path, the arrangement is not limited to this. For example, they may be exchanged in position or both the optical delay means and the phase modulating means may be disposed in one of the optical paths.

The confocal laser scanning optical system (C) has an irradiation optical system composed of a semitransparent mirror 10 and objective lenses 11 and 12, a condenser optical system composed of a lens 13 and a shield plate 14 having a pin hole aperture, a photo multiplier tube 15 as photodetector, and a lockin amplifier for signal processing. The semitransparent mirror 10 transmits the beam from the light modulation optical system (B), and the beam is converged by the objective lenses 11, 12 onto a specimen 20 to form a light spot thereon. Light from the specimen 20 again passes through the objective lenses 11, 12 and is then reflected by the semitransparent mirror 10 to be converged by the lens 13 onto the pin hole aperture in the shield plate 14. Light passing through the pin hole aperture enters the photo multiplier tube 15 as photodetector. The photo multiplier tube 15 outputs a signal depending upon a light quantity of incident light by the photoelectric conversion. The lockin amplifier 16 amplifies only a modulation component with frequency equal to a double of the phase modulation frequency out of the output signal. The shield plate 14 having the pin hole aperture is serving as a space filter for detecting only scattered light or radiation from the focal position of the irradiation optical system. An optical trap 17 is provided for preventing light reflected by the semitransparent mirror 10 out of the light from the light modulation optical system from entering the condenser optical system and from in turn causing stray light.

Scanning means 30 is disposed between the semitransparent mirror 10 and the objective lenses 11, 12 in the irradiation optical system, which is for scanning the specimen 20 with the light spot converged by the optical system 11, 12. The scanning means 30 may be any one conventionally known as optical scanning means utilizing galvanometer or accoustic-optical modulator (AOM), which moves a light spot to scan the specimen at a predetermined speed by a signal from scanning drive means 31. The scanning means 30 can be considered as space modulator, and therefore it could be a device for moving the stage holding the specimen 20 relative to the optical system. The specimen 20 as sample is enclosed in a sample chamber 21 which holds the sample while cooling it with necessity.

Further, the optical measuring apparatus of the present embodiment has recording and reproducing means as electric signal processing unit 40, which can record the output signal from the lockin amplifier 16 in correspondence with a position of light spot of irradiation optical system obtained by monitoring the scanning means 30 and with a delay time by the optical delay means 4 in light modulation optical system and which can reproduce the recorded data with necessity. Also, the apparatus is provided with a data analyzing unit 50 which can analyze a change amount of output signal from electric signal processing unit 40 upon change of delay time of light modulation optical system (or optical delay means 4) at a desired point in the specimen where a light spot is formed by the irradiation optical system.

An arbitrary combination can be chosen with necessity between the laser beam scanning by the scanning means 30 and the change of optical path length by the optical delay means 4, but the relative scanning speed of light spot on the specimen must be sufficiently slower than the phase modulation by the phase modulator. Control unit 32 controls the phase modulation means 5 and the optical delay means 4, and signals therefrom are transmitted to the data analyzing unit 50 through the electric signal processing unit 40. The data analyzing unit 50 analyzes the output signals and displays a desired image.

Using the apparatus of the present embodiment having the structure as described, observation was carried out on an organism tissue stained by a dye, for example by Giemsa, which is a kind of vital staining dye. In the observation, a selected laser wavelength was about 640 nm and the phase modulation frequency of phase modulation means 5 was 20 kHz. While a laser beam was fixed by the scanning means 30 at a point on the specimen 20, the stage position of optical delay means 4 was moved. During the scanning, only an electric signal of 40 kHz was amplified and recorded through the lockin amplifier 16 to obtain an optical phase relaxation time at the laser focus position. Similarly, other optical phase relaxation times were obtained at spatial points on the specimen 20, whereby detailed information was obtained about the organism tissue. The observation confirmed that the present embodiment was effective to measure the physicochemical properties of specimen.

Embodiment 2

Figure 3:
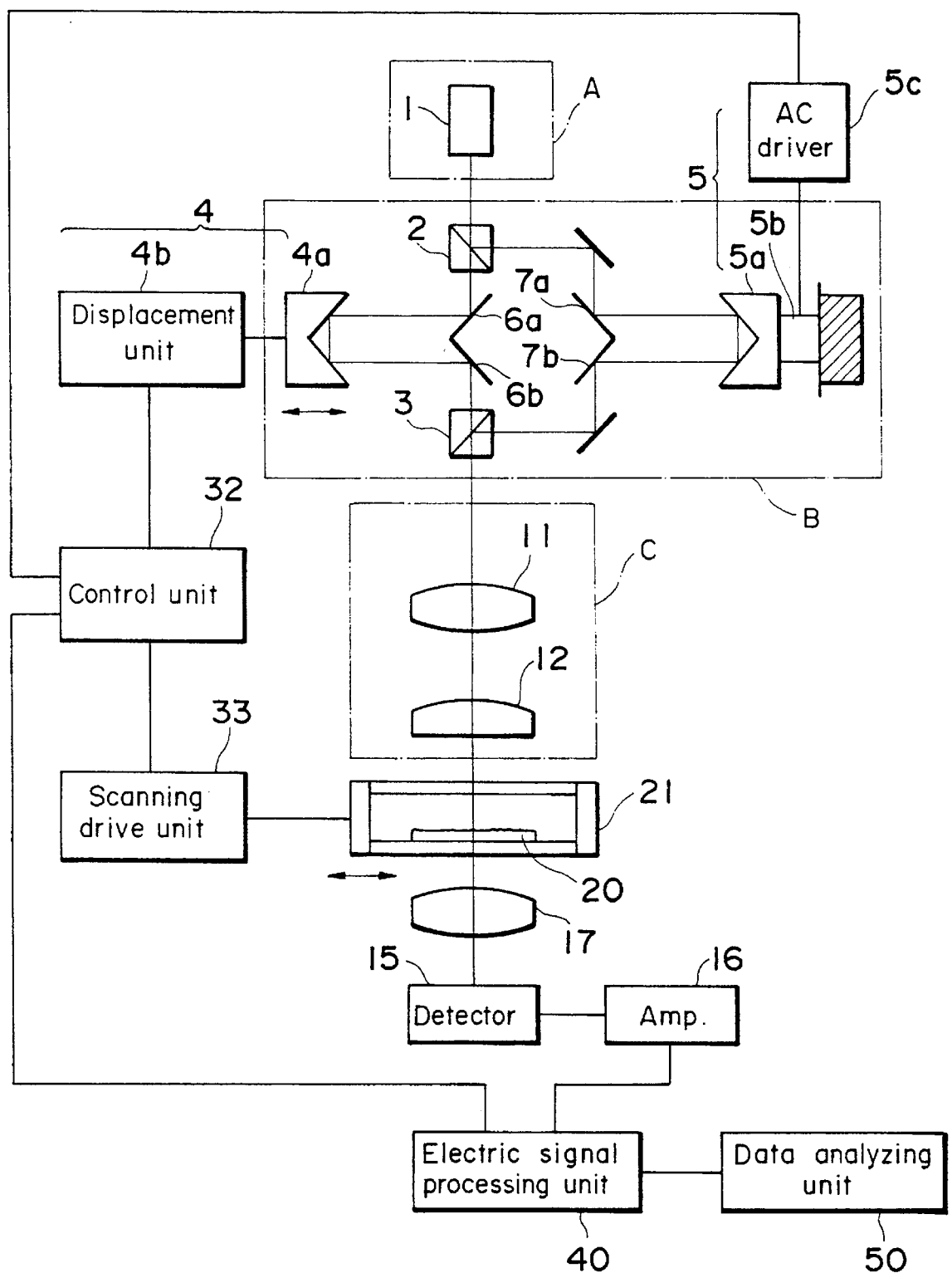
FIG. 3 is an explanatory drawing to show the structure of the second embodiment.

The second embodiment is now described referring to FIG. 3. In FIG. 3, constituent elements denoted by the same numerals as those in FIG. 2 are identical or equivalent to those. The present embodiment is different from the first embodiment shown in FIG. 2 in that the laser scanning optical system (C) does not have a confocal condenser optical system and it is of a transmission type. Further, the light spot scan of irradiation optical system is effected by moving an unrepresented stage for a sample chamber 21 enclosing a specimen 20 by scan drive unit 33. The other portion is constructed in the same manner as in the first embodiment. Transmitted, scattered or radiated light from the specimen 20 is converged by a condenser lens 17 onto a photodetector 15, and a lockin amplifier 16 amplifies only a modulation component with frequency equal to a double of the phase modulation frequency out of the output signal from photodetector 15. The amplified signal is processed as desired by an electric signal processing unit 40 and a data analyzing unit 50.

The arrangement of the second embodiment also permits the detection of optical echo from specimen, whereby the physicochemical information of specimen can be obtained. Since the laser scanning optical system (C) in this embodiment does not have a confocal condenser optical system, the optical measuring apparatus can be compact and simple.

In either of the first and second embodiments, the optical echo with wavelength equal to that of irradiation light was detected by the detector 15. Similarly, optical echo is indirectly measured as intensity of fluorescence emitted from an object to be measured is detected. In this case, intensity modulation component at frequency 2f of fluorescence is detected. In this case, only the optical echo can be of course detected by setting a filter transmitting only a wavelength band of fluorescence in the optical path to the photodetector.

Embodiment 3

Figure 4:
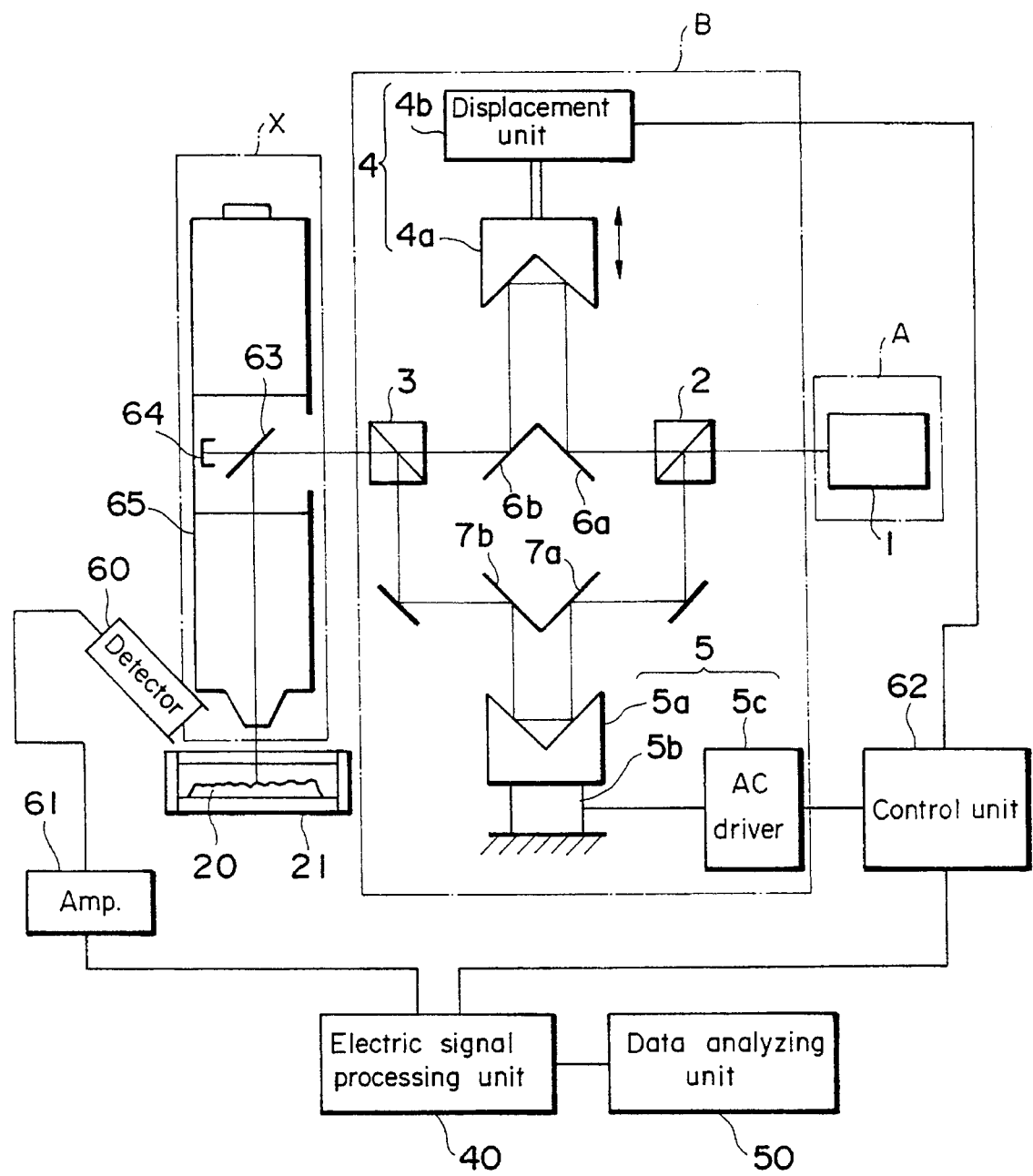
FIG. 4 is an explanatory drawing to show the structure of the third embodiment realizing simplification of structure.

The third embodiment is next described with FIG. 4. The present embodiment relates to a simple optical measuring apparatus which can provide the conventional optical microscopes with a function to measure the physicochemical properties of specimen.

In FIG. 4, the same reference numerals denote the same or equivalent constituent elements as those in FIG. 2 or in FIG. 3. In FIG. 4, a portion (X) surrounded by a dotted line represents the schematic structure of a conventional optical microscope.

The present embodiment applicable to the optical microscope (X) has light source means (A), a light modulation optical system (B), a detector 60 which is a photodetector, a lockin amplifier 61, an electric signal processing unit 40, a data processing unit 50 and control means 62. Signal processing means is constituted by the lockin amplifier 61, the electric signal processing unit 40, the data processing unit 50 and the control means 62.

The light modulation optical system (B) has a light splitter 2, an optical mixer 3, first orthogonal reflection planes 6a, 6b, second orthogonal reflection planes 7a, 7b, a first corner cube 4a fixed to an unrepresented movable stage, a displacement unit 4b which is an optical delay unit, and phase modulation means 5 which is a phase modulator. The phase modulation means 5 has a corner cube 5a, a piezoelectric device 5b and an AC drive power source 5c.

The optical microscope (X) has the general construction with an irradiation optical system comprised of a semitransparent mirror 63, an optical trap 64 and an objective lens system 65.

The light source means (A) in the present embodiment is nothing but a laser beam source 1, which is an 80 MHz mode-locked argon ion laser pumped dye laser. Other lasers may be also used as the laser light source 1, such as the multi-mode semiconductor lasers, the mode-locked semiconductor lasers, the light emitting diodes, and the solid lasers. Light emitted from the laser beam source 1 preferably has a space coherence with which the light source can be assumed as a point on an image plane and has a time coherence shorter than an optical phase relaxation time of a light absorbing band to be watched in specimen.

The laser beam emitted from the laser beam source 1 is guided to enter the light splitter 2 on the input side of the light modulation optical system (B), and the light splitter 2 splits the laser beam into two beams. The optical mixer 3 is located on the output side of the light modulation optical system (B) to mix the thus split beams. Both the light splitter 2 and the optical mixer 3 are polarization beam splitters. A semitransparent mirror having little or no polarization property may be employed instead of the polarization beam splitter. The first orthogonal reflection planes 6a, 6b and the second orthogonal reflection planes 7a, 7b are disposed in parallel between the light splitter 2 and the optical mixer 3. The 2-path interferometer such as the Michelson interferometer and the Mach-Zehnder interferometer is suitable as the optical system for splitting the light from light source means (A) and mixing the split beams as described.

The beam passing through the splitting surface of the light splitter 2 is reflected by one 6a of the first orthogonal reflection surfaces and then travels toward the first corner cube 4a fixed to the unrepresented movable stage. The beam reflected by the corner cube 4a is again reflected by the other 6b of the first orthogonal reflection planes to enter the optical mixer 3. The displacement unit 4b displaces the corner cube 4a through the movable stage. The corner cube 4a, the movable stage and the displacement unit 4b constitute the optical delay means 4. One of the beams can have a certain amount of delay by moving the corner cube 4a by the displacement unit 4b. The corner cube 4a may be replaced by two mirrors or by a right-angle prism.

The beam reflected by the splitting surface of the light splitter 2 is again reflected by one 7a of the second orthogonal reflection planes then to enter the phase modulation means 5. A generally well-known phase modulation means 5 is one using an electrooptical crystal, but the present embodiment employs a piezoelectric device 5b fixed at one end and fixed to the corner cube 5a at the other end. The AC drive power source 5c applies an AC voltage of predetermined frequency f to the piezoelectric device 5d, constituting the phase modulation means of frequency f. The corner cube 5a may be replaced by a right-angle prism with small dispersion. The beam from the phase modulation means 5 is then reflected by the other 7b of the second orthogonal reflection planes to enter the optical mixer 3.

Although the optical delay means 4 is disposed in the transmission light path of the light splitter 2 and the phase modulation means 5 in the reflection optical path in the present embodiment, the arrangement is not limited to this. For example, they may be exchanged in position, or both the optical delay means and the phase modulation means may be disposed in one of the optical paths.

The light modulation optical system (B) is constituted by the light splitter 2, the optical mixer 3, the optical delay means 4 and the phase modulation means 5. The two beams in the light modulation optical system (B) are mixed in the optical mixer 3 then to travel toward the semitransparent mirror 63 in the optical microscope (X).

In the optical microscope (X), the beam from the light modulation optical system (B) is reflected by the semitransparent mirror 63 inclined at an inclination angle of 45° to the optical axis, and the reflected beam is converged by the irradiation optical system comprising the objective lens system 65 onto the specimen 20 to form a light spot thereon. A detector 60 comprising a photo multiplier tube is provided to detect radiation due to fluorescence or phosphorescence, reflected, transmitted, diffracted or scattered light of irradiation laser beam at high sensitivity at the light spot forming portion in the specimen 20. A filter may be inserted in front of the detector 60 with necessity. The detector 60 may be located at any position without being limited to the position as shown, for example at a location where it can detect transmitted light.

The detector 60 outputs a signal depending upon a light quantity of incident light by photoelectric conversion, and the lockin amplifier 61 amplifies only the modulation component with frequency equal to a double of the phase modulation frequency out of the output signal from the detector 60. The amplified signal is stored and analyzed in the data processing unit 50 through the electric signal processing unit 40 in accordance with the delay time by the optical delay means 4. The optical trap 64 is provided for preventing light transmitted through the semitransparent mirror 63 out of the light from the light modulation optical system (B) from entering the condenser optical system and from in turn causing stray light. The sample chamber 21 enclosing the specimen has a function to cool the specimen with necessity.

The observation of configuration through the optical microscope may be done at the same time as the measurement of optical echo or in a consecutive manner while changing over therebetween.

The specimen may be observed at a plurality of locations through the optical echo microscope by manually or mechanically moving the sample chamber. Of course, the detector may be arranged to move.

Using the embodiment as described, observation was carried out with organism tissue stained by a dye for example of Rhodamine 640 or Texas Red. In the observation, a laser beam with wavelength near 600 nm was selected as the laser beam from the laser beam source 1, and the phase modulation frequency of the phase modulation means 5 was 20 kHz. While the configuration of the tissue was observed through the optical microscope (X), an optical phase relaxation time was measured. In more detail, while the laser beam was focused to irradiate a point in field of microscope, the stage position of the optical delay means 4 was moved. During the movement, only an electric signal of 40 kHz was amplified and recorded through the lockin amplifier 61 to obtain an optical phase relaxation time thereat. Thus, more detailed information was obtained in the observation about the organism tissue together with the configuration information. Therefore, the present embodiment enables the measurement of physicochemical properties of specimen simply by combining the apparatus with a conventional microscope, enhancing simplicity.

Embodiment 4

Figure 5:
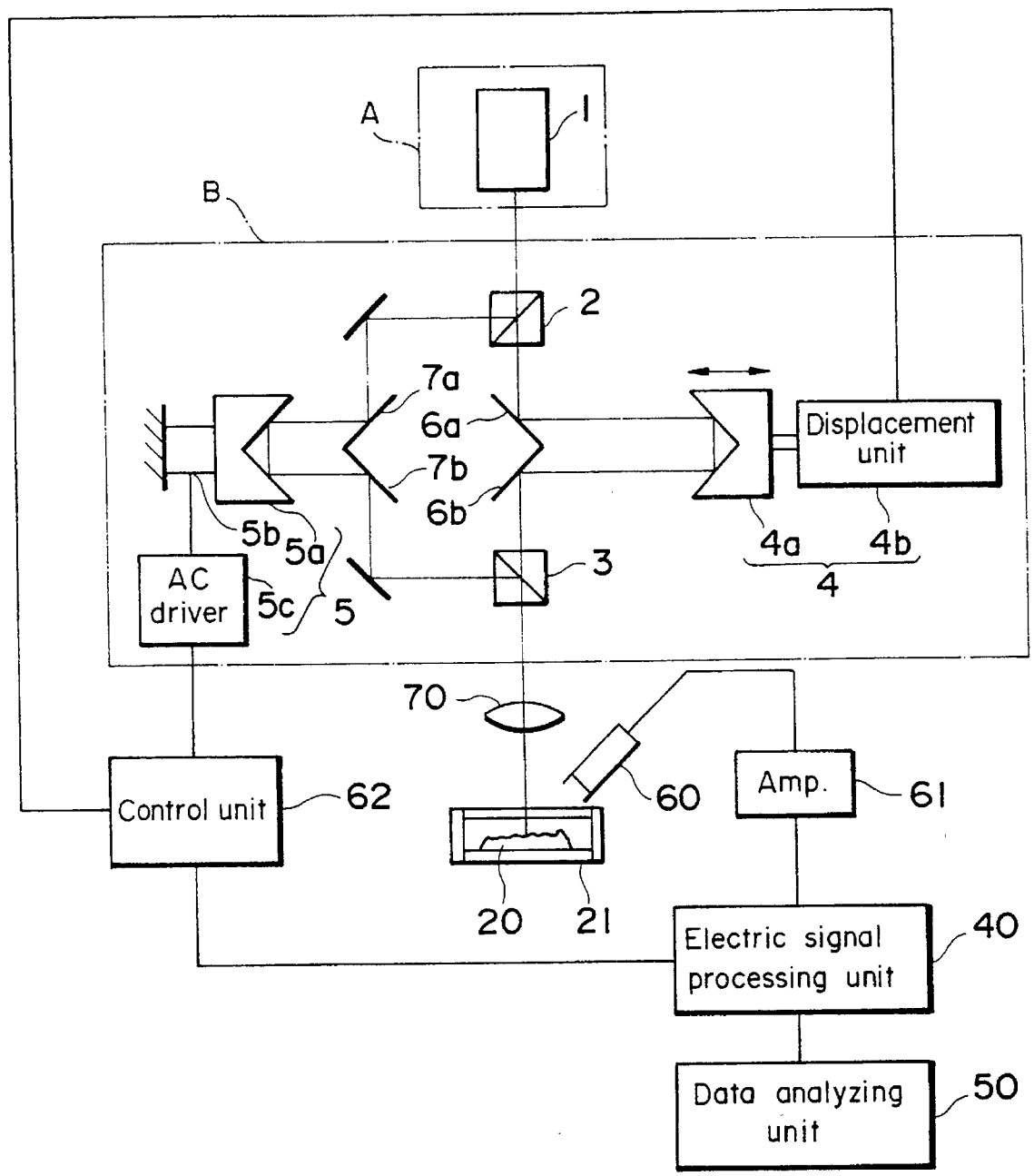
FIG. 5 is an explanatory drawing to show the structure of the fourth embodiment realizing simplification of structure and to show the structure of the fifth embodiment realizing improvement of SN ratio.

The fourth embodiment is described below with FIG. 5. This embodiment relates to a simple optical measuring apparatus. In FIG. 5, the same reference numerals denote the same or equivalent constituent elements as those in FIG. 4.

In FIG. 5, the laser beam emitted from the laser beam source 1 is guided to enter the light splitter 2 on the input side of the light modulation optical system (B), and the light splitter 2 splits the laser beam into two beams. The optical mixer 3 is located on the output side of the light modulation optical system (B) to mix the thus split beams. Both the light splitter 2 and the optical mixer 3 are polarization beam splitters. A semitransparent mirror having little or no polarization property may be employed instead of the polarization beam splitter. The first orthogonal reflection planes 6a, 6b and the second orthogonal reflection planes 7a, 7b are disposed in parallel between the light splitter 2 and the optical mixer 3. The 2-path interferometer such as the Michelson interferometer and the Mach-Zehnder interferometer is suitable as the optical system for splitting the light from light source means (A) and mixing the split beams as described.

The beam passing through the splitting surface of the light splitter 2 is reflected by one 6a of the first orthogonal reflection surfaces and then travels toward the first corner cube 4a fixed to the unrepresented movable stage. The beam reflected by the corner cube 4a is again reflected by the other 6b of the first orthogonal reflection planes to enter the optical mixer 3. The displacement unit 4b displaces the corner cube 4a through the unrepresented movable stage. The corner cube 4a, the movable stage and the displacement unit 4b constitute the optical delay means 4. One of the beams can have a certain amount of delay by moving the corner cube 4a by the displacement unit 4b. The corner cube 4a may be replaced by two mirrors or by a right-angle prism.

The beam reflected by the splitting surface of the light splitter 2 is again reflected by one 7a of the second orthogonal reflection planes then to enter the phase modulation means 5. A generally well-known phase modulation means 5 is one using an electrooptical crystal, but the present embodiment employs a piezoelectric device 5b fixed at one end and fixed to the corner cube 5a at the other end. The AC drive power source 5c applies an AC voltage of predetermined frequency f to the piezoelectric device 5b, constituting the phase modulation means of frequency f. The corner cube 5a may be replaced by a right-angle prism with small dispersion. The beam from the phase modulation means 5 is then reflected by the other 7b of the second orthogonal reflection planes to enter the optical mixer 3.

Although the optical delay means 4 is disposed in the transmission light path of the light splitter 2 and the phase modulation means 5 in the reflection optical path in the present embodiment, the arrangement is not limited to this. For example, they may be exchanged in position, or both the optical delay means and the phase modulation means may be disposed in one of the optical paths.

The light modulation optical system (B) is constituted by the light splitter 2, the optical mixer 3, the optical delay means 4 and the phase modulation means 5. The two beams in the light modulation optical system (B) are mixed in the optical mixer 3 and the mixed beam is guided through a suitable lens system 70 to irradiate the specimen 20 in the sample chamber 21. The sample chamber 21 has a function to cool the specimen with necessity.

A detector 60 comprising a photo multiplier tube is provided to detect radiation due to fluorescence or phosphorescence, reflected, transmitted, diffracted or scattered light of irradiation laser beam at high sensitivity at the light spot forming portion in the specimen 20. A filter may be inserted in front of the detector 60. The position of detector 60 is not limited to the position as shown, but the detector may be located at a position where it can detect transmitted light.

The detector 60 outputs a signal depending upon a light quantity of incident light by photoelectric conversion, and the lockin amplifier 61 amplifies only the modulation component with frequency equal to a double of the phase modulation frequency out of the output signal from the detector 60. The amplified signal is stored and analyzed in the data processing unit 50 through the electric signal processing unit 40 in accordance with the delay time by the optical delay means 4.

The optical histological testing apparatus of the present embodiment as described above was used to inspect specimens of normal human liver tissue and tumor human liver tissue stained by Rhodamine 640, which were clearly discriminated from each other in the inspection. Namely, the apparatus was able to discriminate the normal human liver tissue from the abnormal tissue, enabling the histological test at very high sensitivity. The same result was obtained using Texas Red and its derivatives as staining dye. Also, test was possible with cell samples as specimen as well as the tissue samples. The experimental conditions were as follows: the sample temperature was 5 Kelvin; the laser beam from the laser beam source 1 was a laser beam with wavelength near 600 nm; the phase modulation frequency of phase modulation means 5 was 20 kHz. Moving the stage position of optical delay means 4, only an electric signal of 40 kHz was amplified and recorded through the lockin amplifier 31 to obtain an optical phase relaxation time. An objective inspection result was obtained based on the thus obtained information.

Therefore, the present embodiment can provide a very high sensitive optical histological testing apparatus. The optical histological testing apparatus in this embodiment can detect a fine change in tissue or cell, which the conventional histological testing apparatus failed to detect, so that the histological test can be done at very high sensitivity.

Embodiment 5

The fifth embodiment is next described. This embodiment relates to an optical measuring apparatus which can measure the physicochemical properties of specimen at high precision by detecting the optical echo at high SN ratio. The apparent structure of this embodiment is the same as that in FIG. 5 (the fourth embodiment), and the features of the present embodiment will be described referring to FIG. 5.

A laser beam source 1 employed in the present embodiment emits a beam with central wavelength on the longer wavelength side than a wavelength having the maximum absorption coefficient in wavelength range in a light absorption band of specimen 20. The beam emitted from the laser beam source 1 has a space coherence with which the beam source can be assumed as a point on an image plane and a time coherence shorter than an optical phase relaxation time of a light absorption band of specimen 20 to be watched.

The laser beam source 1 is so arranged that the central wavelength thereof can be changed on the longer wavelength side than the wavelength with maximum absorption coefficient, depending upon the wavelength having the maximum absorption coefficient in the wavelength range in the light absorption band of specimen 20. The central wavelength of irradiation laser may be changed for example by changing the laser dye, by changing the cavity length of laser, or by inserting a birefringent filter into the cavity of laser.

The optical measuring apparatus of the present embodiment as described above was used to inspect specimens of normal human liver tissue and tumor human liver tissue stained by Rhodamine 640. The temperature of specimens was 5 Kelvin. The wavelength having the maximum absorption coefficient was 590 nm in the optical absorption band of Rhodamine 640. The central wavelength of laser was set to about 600 nm, which was longer than the wavelength having the maximum absorption coefficient in the optical absorption band of specimen. The optical echo was measured at very high SN ratio, so that the two samples are clearly discriminated from each other by the obtained phase relaxation times $T_2$. Namely, the normal human liver tissue was discriminated from the abnormal human liver tissue, which enabled the histological test at very high sensitivity. However, when the central wavelength of laser was set to about 580 nm, which was shorter than the wavelength of the maximum absorption coefficient, the optical echo was obtained at very low SN ratio. Similar inspection was carried out using other staining dyes, specifically Texas Red and its derivatives, derivatives of Rhodamine 640, Giemsa dye, methylene blue, azure B, and eosin. Using such staining dyes, the SN ratio was high on the longer wavelength side than the wavelength of the maximum absorption coefficient but low on the shorter wavelength side. The specimens could be cell samples as well as the tissue samples. In the experimental conditions, the phase modulation frequency of phase modulation means 5 was set at 20 kHz. Moving the stage position of the optical delay means 4, only an electric signal of 40 kHz was amplified and recorded through the lockin amp 31 to obtain an optical phase relaxation time. An objective inspection result was obtained based on the thus obtained information.

Although the optical echo was measured using the phase modulation in the present embodiment, the optical echo can be measured by intensity modulation, similarly enabling the measurement at high SN ratio.

Embodiment 6

Figure 6:
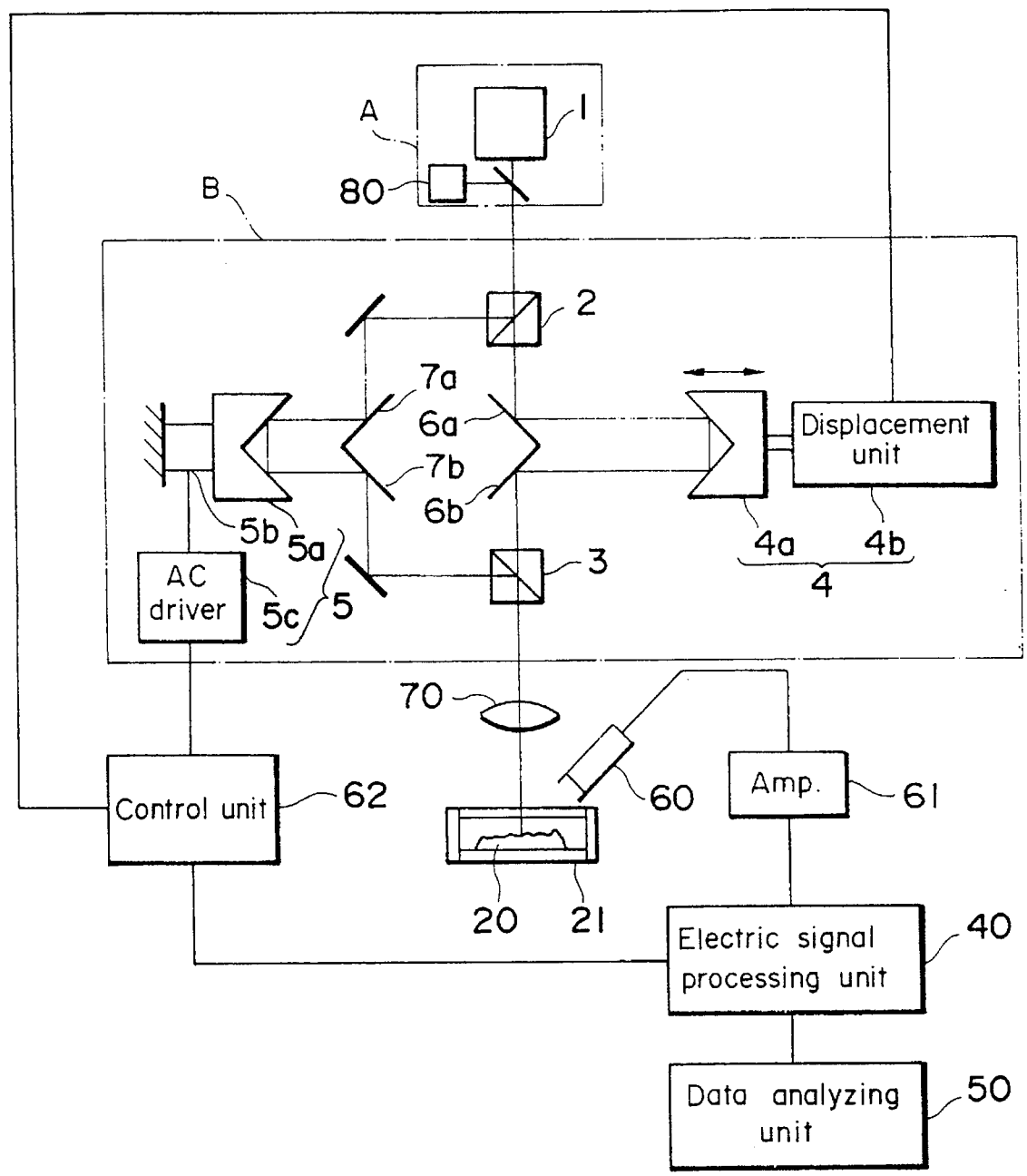
FIG. 6 is an explanatory drawing to show the structure of the sixth embodiment realizing improvement of SN ratio.

The sixth embodiment is described referring to FIG. 6. This embodiment relates to an optical measuring apparatus which can measure the physicochemical properties of specimen at high precision by detecting the optical echo at high SN ratio. In FIG. 6, the same reference numerals denote the same or equivalent constituent elements as those in FIG. 5.

A light source 80 with wide spectrum, such as a halogen lamp, a xenon lamp and a mercury lamp, is used to measure a light absorption spectrum of specimen 20. This light source 80 can be located at the position of laser beam source 1 or at the position of light source 80 as shown in FIG. 6. As the light source 80, a laser beam from the laser beam source 1 or from another laser source may be used after widened in spectrum by self-phase modulation or the like. This light is guided through an unrepresented wavelength scanning apparatus such as a monochromator to irradiate a specimen successively at each wavelength. A detector 60 receives fluorescence emitted from an object 4 to be measured to measure an absorption spectrum. After a spectrum is measured for the specimen 20 through a detector 60 and a data processing unit 50, a wavelength having the maximum absorption coefficient is obtained in wavelength range in light absorption band to be watched.

The other portion of structure is the same as that in the fifth embodiment.

The above measurement can be automatically carried out with a command from the data processing unit 50 to the laser beam source 1.

The apparatus of the present embodiment can measure the wavelength having the maximum absorption coefficient of specimen 20, enabling easy measurement of optical echo at high SN ratio.

Embodiment 7

Figure 7:
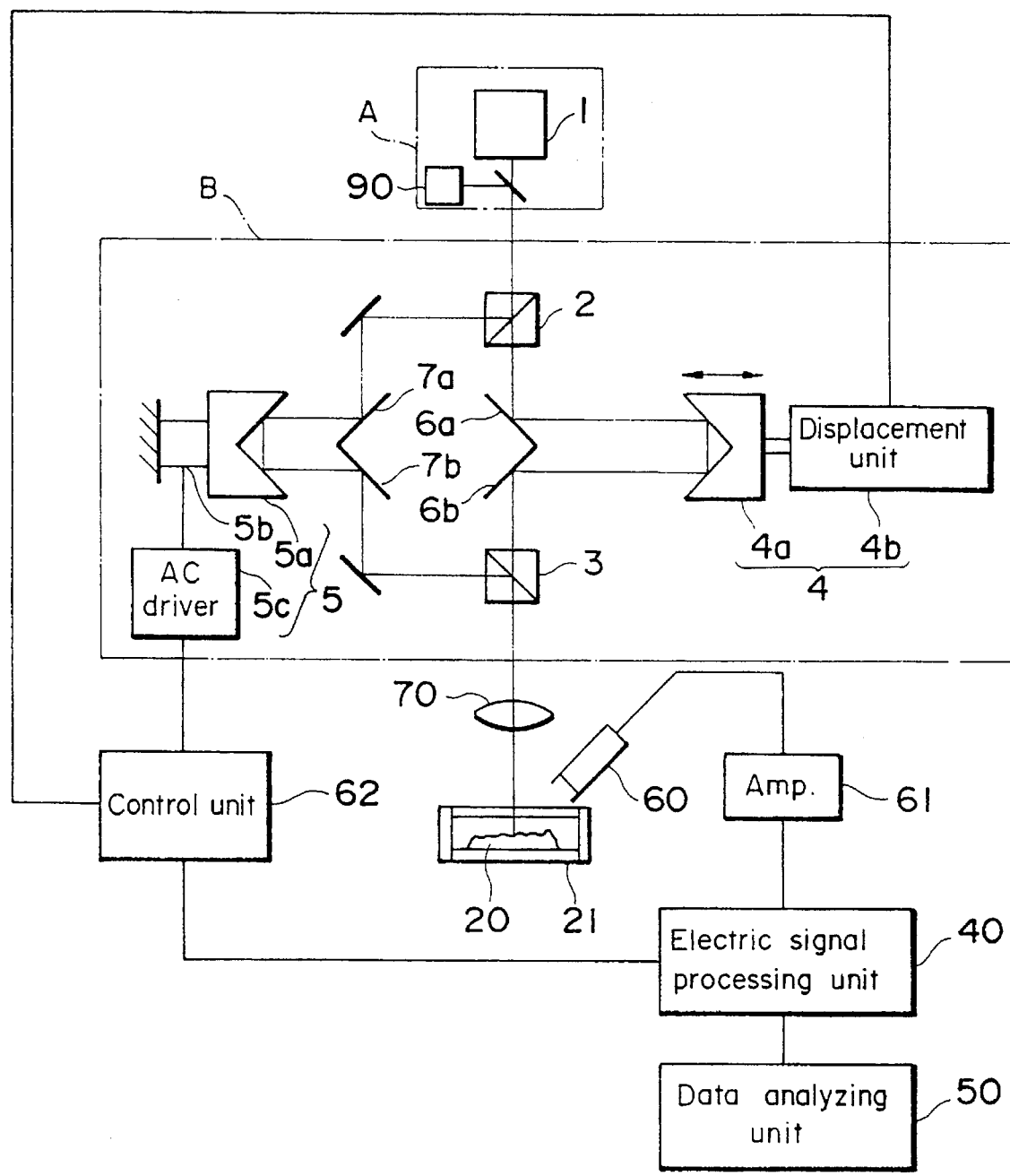
FIG. 7 is an explanatory drawing to show the structure of the seventh embodiment realizing improvement of SN ratio.

The seventh embodiment is next described referring to FIG. 7. This embodiment relates to an optical measuring apparatus which can measure the physicochemical properties of specimen at high precision by detecting the optical echo at high SN ratio. In FIG. 7, the same reference numerals denote the same or equivalent constituent elements as those in FIG. 6.

The present embodiment provides a high-precision optical measuring apparatus which was attained by removing a disadvantageous phenomenon (phenomenon disadvantageous in increasing the SN ratio) recognized in development of a higher SN ratio optical measuring apparatus.

When the light source is a laser with relatively narrow wavelength band such as the semiconductor laser, influence of previously irradiated laser beam remains in specimen. It was observed that this remaining influence caused a problem that the optical echo could not be detected at high SN ratio in next measurement or in continuous measurement.

In more detail, the influence of such laser beam (first beam) is such that a persistent spectral hole is formed relatively deep at the laser irradiated wavelength in the wavelength range of light absorption band of specimen and that the influence of spectral hole remains when the specimen is irradiated by next laser beam. It was found that the influence caused the SN ratio to drop in optical echo detection.

It was then considered that the influence of the laser beam (first beam) previously irradiating the specimen could be removed by eliminating the permanent optical hole formed by the previous irradiation. Finding was that the permanent hole could be eliminated by inducing reverse reaction of permanent hole formation or rearrangement of photo reactive molecules under irradiation of light (second beam) having a spectrum ranging over the almost entire region of light absorption band of specimen or under irradiation of light (second beam) ranging over the light absorption band of photo reaction product newly produced by the permanent hole formation and that the permanent hole could be eliminated by inducing relocation of photo reactive substance, or under irradiation of light having a shorter wavelength than the first beam. Accordingly, the present invention employs an erasing light source (second light source) for reducing the influence of previous irradiation in addition to a laser beam source (first light source) for optical echo detection.

Therefore, the optical echo can be detected at high SN ratio so as to enable the high-precision optical inspection by inducing the reverse reaction of permanent hole formation or rearrangement of photoreactive molecules under irradiation of light (second beam) having a spectrum covering almost entire range of light absorption band of specimen, under irradiation of light covering the light absorption band of photo reaction product newly produced by the permanent hole formation, or under irradiation of light (second beam) with shorter wavelength than the first beam.

The structure of the apparatus is described below in detail with reference to FIG. 7. The apparatus is constituted by two portions respectively encircled by a dotted line, that is, light source means (A) and light modulation optical system (B). The light source means (A) of the present embodiment includes a light source 1 (first light source) and an erasing light source 90 (second light source). The light source 1 (first light source) is an 80 MHz mode-locked argon ion laser pumped dye laser. Other lasers may be employed as the light source 1 (first light source), such as the multi-mode semiconductor lasers, the mode-locked semiconductor lasers, the light emitting diodes, and the solid lasers. Light (first beam) emitted from the light source 1 (first light source) preferably has a space coherence with which the light source can be assumed as a point on an image plane and a time coherence shorter than an optical phase relaxation time of a light absorption band of specimen 20 to be watched. The position of erasing light source 90 (second light source) is not limited to the position as shown in FIG. 7, but may be located at any position where the erasing light (second beam) can be arranged to irradiate the specimen 20.

In FIG. 7, the laser beam (first beam) emitted from the laser beam source 1 (first light source) is guided to enter the light splitter 2 on the input side of the light modulation optical system (B), and the light splitter 2 splits the laser beam (first beam) into two beams. The optical mixer 3 is located on the output side of the light modulation optical system (B) to mix the thus split beams. Both the light splitter 2 and the optical mixer 3 are polarization beam splitters. A semitransparent mirror having little or no polarization property may be employed instead of the polarization beam splitter. The first orthogonal reflection planes 6a, 6b and the second orthogonal reflection planes 7a, 7b are disposed in parallel between the light splitter 2 and the optical mixer 3. The 2-path interferometer such as the Michelson interferometer and the Mach-Zehnder interferometer is suitable as the optical system for splitting the light from light source means (A) and mixing the split beams as described.

The beam passing through the splitting surface of the light splitter 2 is reflected by one 6a of the first orthogonal reflection surfaces and then travels toward the first corner cube 4a fixed to the unrepresented movable stage. The beam reflected by the corner cube 4a is again reflected by the other 6b of the first orthogonal reflection planes to enter the optical mixer 3. The displacement unit 4b displaces the corner cube 4a through the movable stage. The corner cube 4a, the movable stage and the displacement unit 4b constitute the optical delay means 4. One of the beams can have a certain amount of delay by moving the corner cube 4a by the displacement unit 4b. The corner cube 4a may be replaced by two mirrors or by a right-angle prism.

The beam reflected by the splitting surface of the light splitter 2 is again reflected by one 7a of the second orthogonal reflection planes then to enter the phase modulation means 5. A generally well-known phase modulation means 5 is one using an electrooptical crystal, but the present embodiment employs a piezoelectric device 5b fixed at one end and fixed to the corner cube 5a at the other end. The AC drive power source 5c applies an AC voltage of predetermined frequency f to the piezoelectric device 5d, constituting the phase modulation means of frequency f. The corner cube 5a may be replaced by a right-angle prism with small dispersion. The beam from the phase modulation means 5 is then reflected by the other 7b of the second orthogonal reflection planes to enter the optical mixer 3.

Although the optical delay means 4 is disposed in the transmission light path of the light splitter 2 and the phase modulation means 5 in the reflection optical path in the present embodiment, the arrangement is not limited to this. For example, they may be exchanged in position, or both the optical delay means and the phase modulation means may be disposed in one of the optical paths.

The light modulation optical system (B) is constituted by the light splitter 2, the optical mixer 3, the optical delay means 4 and the phase modulation means 5. The two beams in the light modulation optical system (B) are mixed in the optical mixer 3 and the mixed light is guided through a proper irradiation optical system 70 to irradiate the specimen 20 in a sample chamber 21. The irradiation optical system 70 may be also used in common as objective optical system in optical microscope. In such an arrangement, an eyepiece optical system is separately provided to form an optical microscope, which enables visual observation. Further, an optical echo microscope which is of the laser scanning microscope type may be obtained by providing another optical system confocal with the irradiation optical system, providing a photodetector before which a pin hole is set, and combining the sample chamber 21 with a movable stage. The sample chamber 21 can be cooled with necessity.

A detector 60 comprising a photo multiplier tube is provided for detecting radiation due to fluorescence or phosphorescence, reflected, diffracted or scattered light of irradiation laser beam at high sensitivity at a light spot forming portion in specimen 20. A filter may be inserted in front of the detector 60 with necessity. The position of detector 60 is not limited to the position shown, but the detector 60 may be located at a position where it can detect transmitted light.

The detector 60 outputs a signal depending upon a light quantity of incident light by photoelectric conversion, and the lockin amplifier 61 amplifies only the modulation component with frequency equal to a double of the phase modulation frequency out of the output signal from the detector 60. The amplified signal is stored or analyzed in the data processing unit 50 through the electric signal processing unit 40 in accordance with the delay time by the optical delay means 4.

The erasing light source 90 (second light source) is a lamp selected from the halogen lamp, the xenon lamp and the mercury lamp. The lamp may be combined with a wavelength selecting element such as a filter and a monocromator. The erasing light source 90 may be a light emitting diode, a dye laser, a gas laser or a solid laser, and may be a combination thereof with a wavelength selecting element if desired. The wavelength of erasing light (second light) may be determined depending upon the specimen 20.

The erasing light source 90 (second light source) normally includes a wide range of wavelength components including the light absorption band of specimen 20 to be watched. If necessary, the wavelength range of erasing light may be selected to match the light absorption band of specimen 20 on the shorter wavelength side than the wavelength of measuring laser beam (first beam). The erasing light (second beam) may be set to irradiate the specimen 20 after measurement of optical echo at a delay time and before measurement of optical echo at a next delay time, or the erasing light may be set to preliminarily irradiate the specimen 20 before measuring the optical echo.

The optical testing apparatus as described above was used to inspect specimens 20 of normal human liver tissue and tumor human liver tissue stained by Rhodamine 640. The wavelength bandwidth of dye laser (first light source) was set to about 2 nm and the center wavelength was about 590 nm. The temperature of specimen was 5 Kelvin. The erasing light (second beam) was light from a halogen lamp combined with a filter for removing light in infrared range, and the irradiation intensity was 100 mW/cm$^2$. The specimen was irradiated for ten seconds with the erasing light (second beam) after measurement at a delay time and before measurement at another delay time. The normal tissue could be clearly discriminated from the tumor tissue by phase relaxation times $T_2$ thereof obtained in the series measurements. Namely, the apparatus was able to distinguish whether the human liver tissue was normal or abnormal, enabling histological inspection at very high sensitivity. Measurement without erasing light (second beam) showed a very low SN ratio of obtained optical echo. Similarly, with staining dyes such as Texas Red and its derivatives, derivatives of Rhodamine 640, Giemsa dye, methylene blue, azure B and eosin, the SN ratio was very low without erasing light (second beam) if the wavelength bandwidth of irradiation laser (first light source) was below several nm. The specimen could be a cell sample as well as the tissue sample. In the experimental conditions, the phase modulation frequency of phase modulation means 5 was 20 kHz. Only an electric signal of 40 kHz was amplified and recorded through the lockin amplifier 10 to obtain an optical phase relaxation time. An objective test result was obtained based on the information.

Although the optical measuring apparatus in the present embodiment detects the optical echo by optical phase modulation technique, the detection of optical echo is not limited to it For example, the optical echo was similarly detected at high SN ratio when the erasing light (second beam) was applied in an optical measuring apparatus which measured the optical echo by intensity modulation technique.

In the present embodiment, the specimen may be irradiated by the erasing light (second beam) before measurement.

As described above, the present embodiment can reduce the influence, which was caused in specimen by light (first beam and other light than the first beam), by irradiating the specimen with erasing light (second beam), whereby the optical echo can be detected at higher SN ratio to enable high-precision optical inspection. Also, a difference can be detected in physicochemical properties of specimen at very high sensitivity.

Embodiment 8

Figure 8:
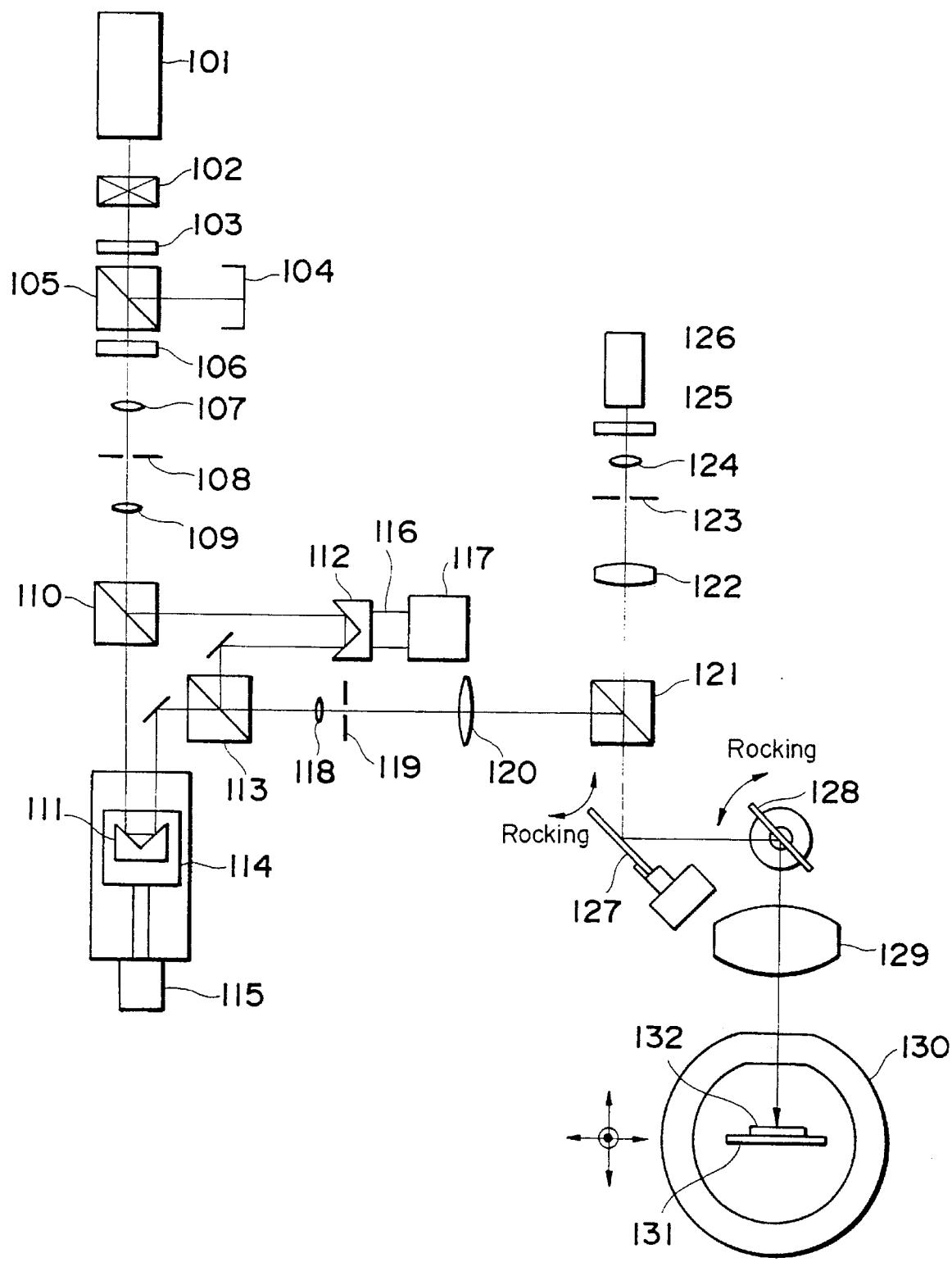
FIG. 8 and FIG. 9 are explanatory drawings to show the structure of the eighth embodiment with two-dimensional scanning mechanism.
Figure 9:
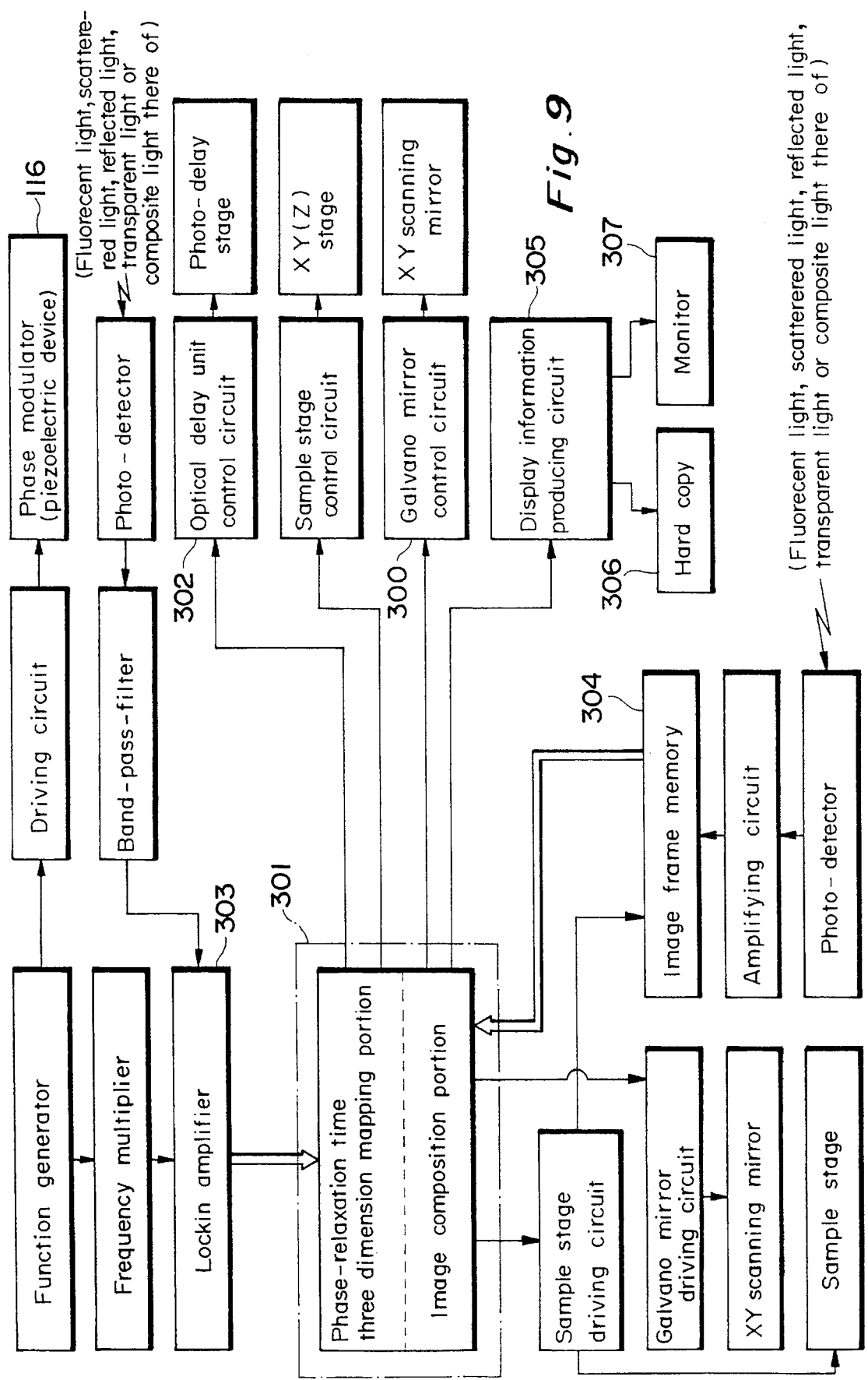

The eighth embodiment is described referring to FIG. 8 and FIG. 9. In this embodiment the apparatus is provided with two-dimensional scanning mechanism for measuring a specimen not only in a limited portion but also in a broad area.

First described with numerals in FIG. 8 are constituent elements of optical measuring apparatus in the present embodiment. There are arranged along the direction of light emission from a light source 101, a shutter 102, a half-wave plate 103, a light splitter 105 composed of a polarization beam splitter with a beam stopper 104 attached thereto, a half-wave plate 106, a lens 107, a pin hole 108, a lens 109, and a light splitter 110 composed of a polarization beam splitter or non-polarization beam splitter. A first corner cube 111 is disposed along the direction of one outgoing beam from the light splitter 110 and a second corner cube 112 along the direction of the other outgoing beam therefrom. An optical mixer 113 is arranged to mix the beams from the first and second corner cubes 111 and 112. The first corner cube 111 is fixed to a sliding stage 114, and the sliding stage 114 is moved by a displacer 115 consisting of a drive motor or an actuator. Meantime, the second corner cube 112 is fixed to a piezoelectric device 116. The piezoelectric device 116 vibrates under application of AC voltage of predetermined frequency f supplied from an AC drive power source 117, which results in vibrating the second corner cube 112 so as to phase-modulate a beam at frequency f.

There are arranged along the direction of outgoing beam from the optical mixer 113, a lens 118, a pin hole 119, a lens 120 and a semitransparent mirror 121. Arranged along the direction of incident beam into or the other outgoing beam from the semitransparent mirror 121 are a Y scan mirror (plane mirror variable in rotation angle in the Y-coordinate direction) 127, an X scan mirror (plane mirror variable in rotation angle in the X-coordinate direction) 128 and an objective lens system 129. Further, a sample table 131 is provided in a cryostat 130 to face the objective lens system 129. A specimen 132 is set on the sample table 131 in measurement as opposed to the objective lens system 129. Arranged along the direction of one outgoing beam from the semitransparent mirror 121 are a lens 122, a pin hole 123, a lens 124, an optical filter 125, and a photodetector 126 such as a photomultiplier tube (PMT) and a photodiode.

The functions of respective constituent elements and the operation of the entire apparatus are further described in detail.

The light source 101 in the present embodiment is nothing but a laser beam source, and the laser beam source 101 is a dye laser pumped by 78 MHz mode-locked argon ion laser. The laser beam source 101 may be one selected from the multi-mode semiconductor lasers, the mode-locked semiconductor lasers, the light emitting diodes, the solid lasers such as Ti: $Al_2O_3$ laser, and general light sources such as a halogen lamp and a noble gas lamp.

The laser beam source 101 has an center wavelength selected to cause resonance with a light absorption band of specimen 132 to be watched. However, some circumstances permit more accurate measurement if the center wavelength is selected on the longer wavelength side than the wavelength having the maximum absorption coefficient in light absorption band of specimen 132 to be watched. Therefore, the center wavelength should be properly selected depending upon the measurement circumstance. A beam emitted from the laser beam source 101 has a space coherence with which the light source can be assumed as a point light source on an image plane and a time coherence shorter than an optical phase relaxation time $T_2$ of the light absorption band of specimen 132 to be watched. It is preferable for some cases to provide a special filter composed of a lens 107, a pin hole 108 and a lens 109. The half-wave plate 103, the beam stopper 104 and the polarization beam splitter 105 are optical components for adjusting a light intensity of incident light into the specimen 132. Although the corner cubes 111 and 112 are used in the present embodiment, they may be replaced by right-angle prisms or retroreflectors.

A laser beam generated by the laser beam source 101 is guided to enter the light splitter 110, which splits the laser beam into two beams. One of the split beams enters the first corner cube 111 while the other beam enters the second corner cube 112.

The corner cube 111, the movable stage 114 and the displacer 115 constitute optical delay means, which delays the beam by a certain amount when the displacer 115 moves the corner cube 111. When an AC voltage of predetermined frequency f supplied from the AC drive power source 117 is applied to the piezoelectric device 116, the piezoelectric device 116 vibrates to phase-modulate the beam at frequency f.

Then, the delayed beam and the phase-modulated beam are mixed with each other in the optical mixer 113. The 2-path interferometer such as the Michelson interferometer and the Mach-Zehnder interferometer is preferable as the optical system for splitting the beam from light source 101 and again mixing the split beams.

Although the optical delay means is provided in the transmission light path of light splitter 110 and the phase modulation means in the reflection light path thereof in the constitution as shown, the arrangement is not limited to it. For example, the two means may be exchanged in position, or the optical delay means and the phase modulation means both may be located in one of the optical paths.

The beam mixed in the optical mixer 113 enters the semitransparent mirror 121. The space filter composed of the lens 118, the pin hole 119 and the lens 120 is provided with necessity. Such a space filter may be arranged also to serve as beam collimator and beam expander if necessary. The semitransparent mirror 121 may be replaced by a dichroic mirror or a beam splitter.

The beam reflected by the semitransparent mirror 121 is first reflected by the Y scan mirror 127 and further reflected by the X scan mirror 128. Therefore, the Y scan mirror 127 and the X scan mirror 128 constitute a two-dimensional beam scanning system. The Y scan mirror 127 and the X scan mirror 128 are galvanomirrors with respective rotation axes being perpendicular to each other in the present embodiment. Alternatively, the two-dimensional beam scanning mechanism may be constituted by a galvanomirror and an acousto-optical modulator or by acousto-optical modulators.

The Y scan mirror 127 and the X scan mirror 128 deflect the beam in a desired spatial direction, and the deflected beam is guided through the objective lens system 129 to be focused onto or into the specimen 132. The cryostat 130 is provided to cool the specimen 132 down to a target temperature suitable for measurement. The sample table 131 is provided with a moving mechanism which can move the table relative to the objective lens system 129. If the sample table 131 is fixed to the cryostat 130 for example, a moving stage (not shown) should be provided for moving the cryostat 130 in three dimensions. Alternatively, the objective lens 129 may be moved in the direction of optical axis. In case that the objective lens 129 is moved in the direction of optical axis (in the direction of arrows), the objective lens 129 is mounted on a moving stage (not shown) for moving it in the direction of optical axis. Such moving stages should be arranged to electrically control a displacement amount thereof by a motor or piezoelectric device.

The laser beam focused on or in the specimen 132 induces electromagnetic waves (reflected light, scattered light, fluorescence or phosphorescence, various scattered light produced by nonlinear optical effect, radiation, etc.). The electromagnetic waves pass through the objective lens 129, the X scan mirror 128 and the Y scan mirror 127 then to enter the semitransparent mirror 121. Only a beam transmitted by the semitransparent mirror 121 passes through the lens 122 and then to be focused on the pin hole 123. Adjustment is made for the pin hole 123, the lens 122, the semitransparent mirror 121, the Y scan mirror 127, the X scan mirror 128 and the objective lens system 129 so that the focal point on the specimen 132 is conjugate with the imaging point on the pin hole 123. Therefore, when the two-dimensional scanning mirror system moves to displace the focal position on the specimen 132, the imaging point does not move on the pin hole 123.

The photodetector 126 receives only electromagnetic waves passing through the pin hole 123. The filter 125 may be inserted with necessity. In case that the photodetector 126 detects weak light different in wavelength from the excitation laser beam, the semitransparent mirror 121 had better be replaced by a dichroic mirror, and the filter 125 by a sharp cut filter. Other alternatives will do. In case that the photodetector 126 detects light with the same wavelength as the excitation laser beam, the filter 125 may be omissible in some cases.

Next described referring to FIG. 9 is the basic signal processing operation in the optical measuring apparatus of the present embodiment. It should be noted that the arrangement shown in FIG. 9 is only an example and that the processing method is not limited to this method. The Y scan mirror 127 and the X scan mirror 128 are set at respectively desired angles by a galvanomirror control circuit 300 in order to obtain an optical echo signal from a point in space in the specimen 132. The sample table 131 and the objective lens system 129 are also controlled to be fixed at respectively desired positions with necessity. The position signals and angle signals are sent to a central control unit (computer) 301 and stored therein. Before this, the piezoelectric device 116 has been driven by the AC voltage of predetermined, frequency f and amplitude. The drive voltage is set as to have no sign change within a cycle. The stage 114 for optical delay is fixed to provide a desired delay time t by the optical delay unit control circuit 302, and a position signal thereof is sent to the central control unit 301 and stored therein. The photodetector 126 outputs a signal depending upon a light quantity of incident light by photoelectric conversion, and a lockin amplifier 303 amplifies only a modulation component with frequency equal to a double of the phase modulation frequency f out of the output signal from the photodetector 126. The amplified signal is stored in the central control unit 301 in correspondence with (in one-to-one correspondence with) the position signals at this moment and the delay time $\tau$ by the movable stage 114 for optical delay.

Then, keeping the focusing point of laser beam fixed, the movable stage 114 is successively moved and stopped, and outputs from the lockin amplifier 303 are stored in correspondence with the position signals and the delay times $\tau$. Thus, outputs from lockin amplifier 303 are stored corresponding to different delay times $\tau$ for a fixed point in specimen 132. A phase relaxation time $T_2$ at this point can be obtained by measuring a degree of decrease of output from lockin amplifier 303 with respect to increase of delay time $\tau$. Normally, the output from lockin amplifier exponentially decreases with increase of delay time $\tau$. Accordingly, the logarithm of output from lockin amplifier 303 is plotted to the delay time $\tau$, and the phase relaxation time $T_2$ is obtained as a slope. This calculation process is carried out by a program in the central control unit 301.

In the next place, the Y scan mirror 127, the X scan mirror 128, and at least one of the sample table 131 and the objective lens system 129 are moved to another position or angle and stopped there, and the process to successively move and stop only the movable stage 114 is again repeated to repeat the measurement as described above. This operation can provide phase relaxation times $T_2$ measured at a plurality of different positions in specimen 132. The thus obtained data is stored in the central control unit 303.

Although in the above description the data is stored while the delay time $\tau$ is changed at a fixed position on the specimen 132, the relation may be reversed. For example, the measurement position may be changed on the specimen 132 while the delay time $\tau$ is kept constant.

Meanwhile, in order to obtain an ordinary image of scanning confocal microscope for the specimen 132, the Y scan mirror 127 and the X scan mirror 128 are controlled such that the laser spot can scan the entire area over the specimen 132 to be observed, and the position signal and the DC output of photodetector 126 are directly recorded in an image frame memory 304. Before this operation, the movable stage 114 has been moved and stopped such that the delay time $\tau$ becomes sufficiently longer than the time corresponding to an inverse of spectrum of light source (electric field correlation time). In this operation, the piezoelectric device 116 may or may not be driven by AC voltage.

A display information producing circuit 305 properly combines phase relaxation times $T_2$ for three-dimensional space thus stored in the central control unit 301 with three-dimensional image signals by the scanning confocal microscope, and the combined data is supplied to a hard copy system 306 or to a monitor 307 for evaluation of specimen 132.

As described above, this embodiment permits the measurement of physicochemical properties of specimen over a broad area on the specimen 132, as well as the observation of image of specimen 132 as in ordinary optical microscopes.

Embodiment 9

Figure 10:
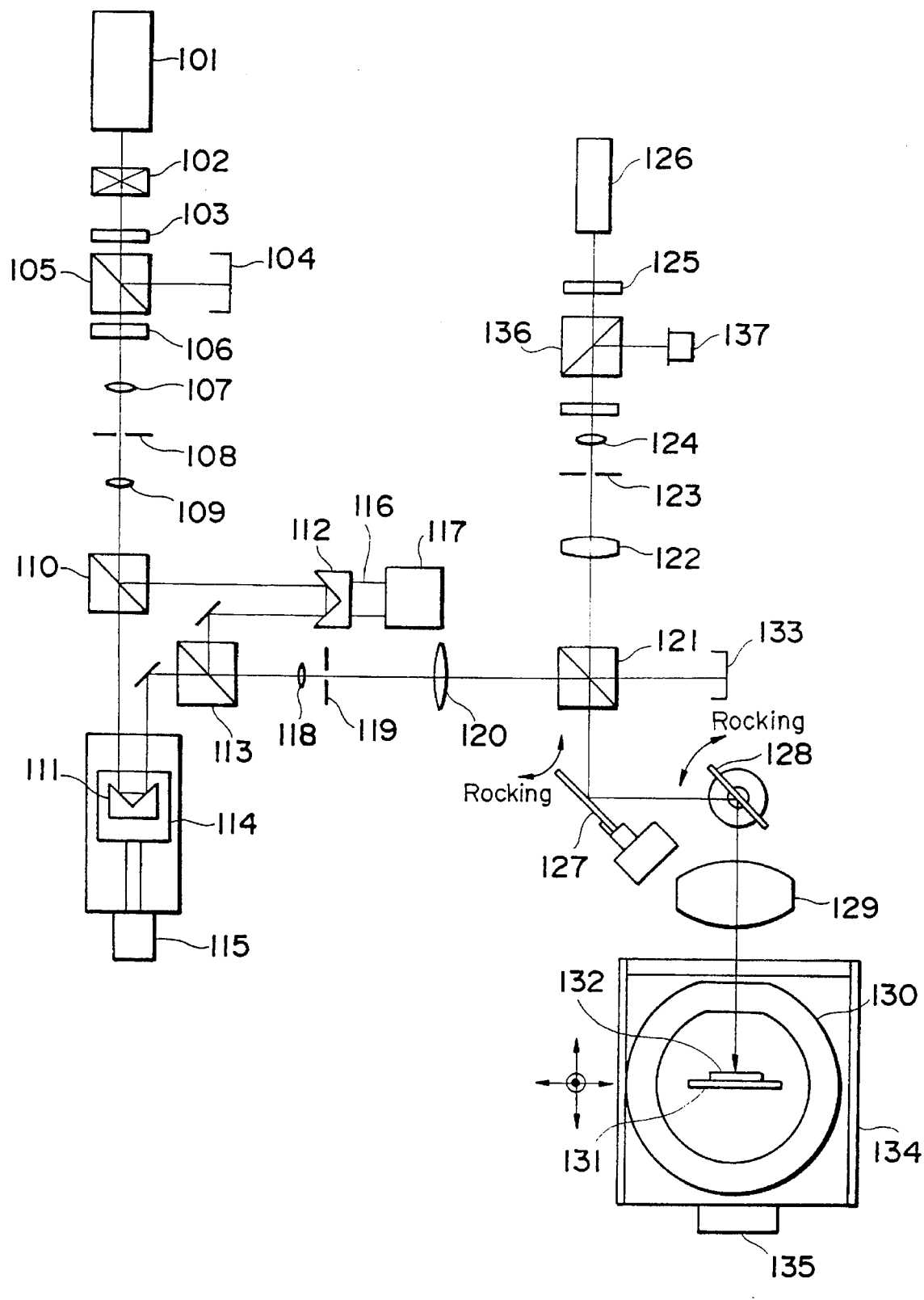
FIG. 10 to FIG. 17 are explanatory drawings to show the structure of each of the ninth to seventeenth embodiments with two-dimensional scanning mechanism.

The ninth embodiment is described referring to FIG. 10. This embodiment is provided with a two-dimensional scanning mechanism for measuring a specimen not only in a small region but also in a broad area. In FIG. 10, the same reference numerals denote the same or equivalent constituent elements as those in FIG. 8. In the present embodiment, a beam stopper 133 is attached to a semitransparent mirror or beam splitter 121, a cryostat 130 is fixed to a stage 134, which is movable back and forth relative to an objective lens system 129 (in the Z direction), and the stage 134 is arranged to be moved by a drive motor (or actuator) 135. Also, a semitransparent mirror 136 is disposed in an optical path between a lens 124 and a filter 125 so that a photodetector 137 such as a photodiode can detect a split beam. Namely, the separate photodetectors 126, 137 receive an image of scanning confocal microscope or an optical echo signal. The semitransparent mirror 136 may be replaced by a beam splitter or a dichroic mirror depending upon the purpose. Specifically, if the phase relaxation time $T_2$ is measured by detecting fluorescence by the photodetector 126, the photodetector 126 should be a sharp cut filter absorbing the laser beam but transmitting fluorescence, the semitransparent mirror 136 a dichroic mirror transmitting fluorescence but reflecting the laser beam, and the photodetector 137 a photodetector detecting scattered light or reflected light from the specimen 132.

Also, if the semitransparent mirror 136 is replaced by a beam, splitter and if a filter similar to the filter 125 is inserted between the semitransparent mirror 136 and the photodetector 137, a fluorescent image of specimen 132 may be obtained by the scanning microscope. In this embodiment, the cryostat 130 is fixed on the Z-axis stage 134 electrically driven.

Embodiment 10

Figure 11:
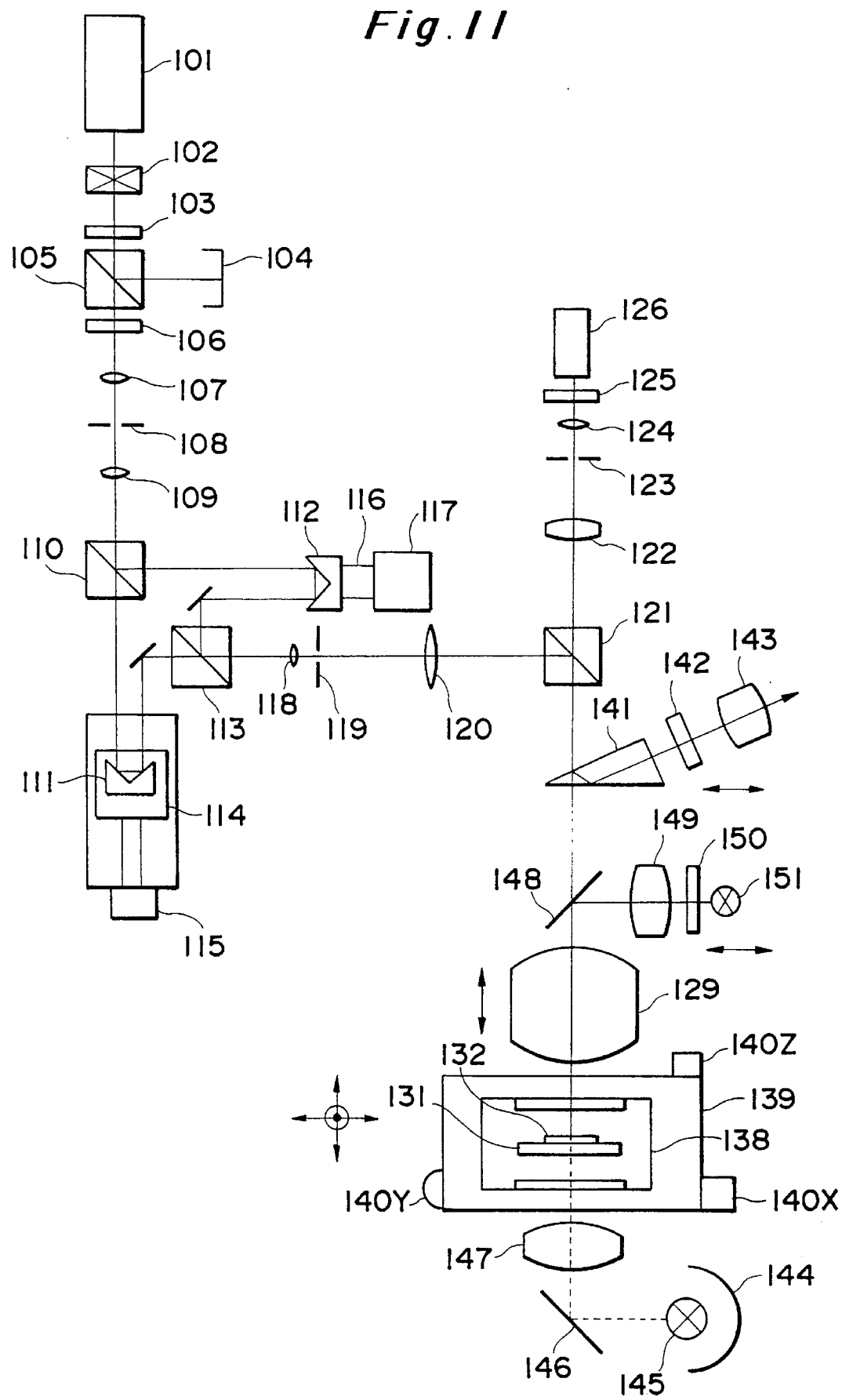

The tenth embodiment is described referring to FIG. 11. This embodiment is provided with a two-dimensional scanning mechanism for measuring the specimen not only in a small region but also in a broad area. In FIG. 11, the same reference numerals denote the same or equivalent constituent elements as those in FIG. 8. The present embodiment does not employ the space scan by the Y scan mirror (galvanomirror) 127 and the X scan mirror (galvanomirror) 128 in FIG. 8. Instead, a double-side windowed cryostat 138 and a sample table 131 are held by an XYZ stage 139 driven by an electric motor working in the X, Y, Z coordinate directions or by actuators 140X, 140Y, 140Z. A microscope image of specimen 132 may be observed with necessity by inserting a prism 141 for sample observation into the optical axis so that the image can be observed directly by bare eye through an eyepiece lens system provided with a filter 142 and a lens 143 or by an electronic image pickup device through an additional optical system.

A first illumination system for illuminating the specimen 132 from the back side thereof to provide transmission light is constituted by a curved mirror 144, a light source 145, a plane mirror 146 and a lens 147, and a second illumination system composed of a beam splitter (or semitransparent mirror) 148, a lens 149, a filter 150 and a light source 151 aligned with the optical system is provided on the object lens system (129) side.

Accordingly, a transmission image of specimen 132 can be observed through the eyepiece lens system or the like as described above under illumination by the first illumination system, while a reflection image of specimen 132 may be observed through the eyepiece lens system or the like under illumination by the second illumination system.

Embodiment 11

Figure 12:
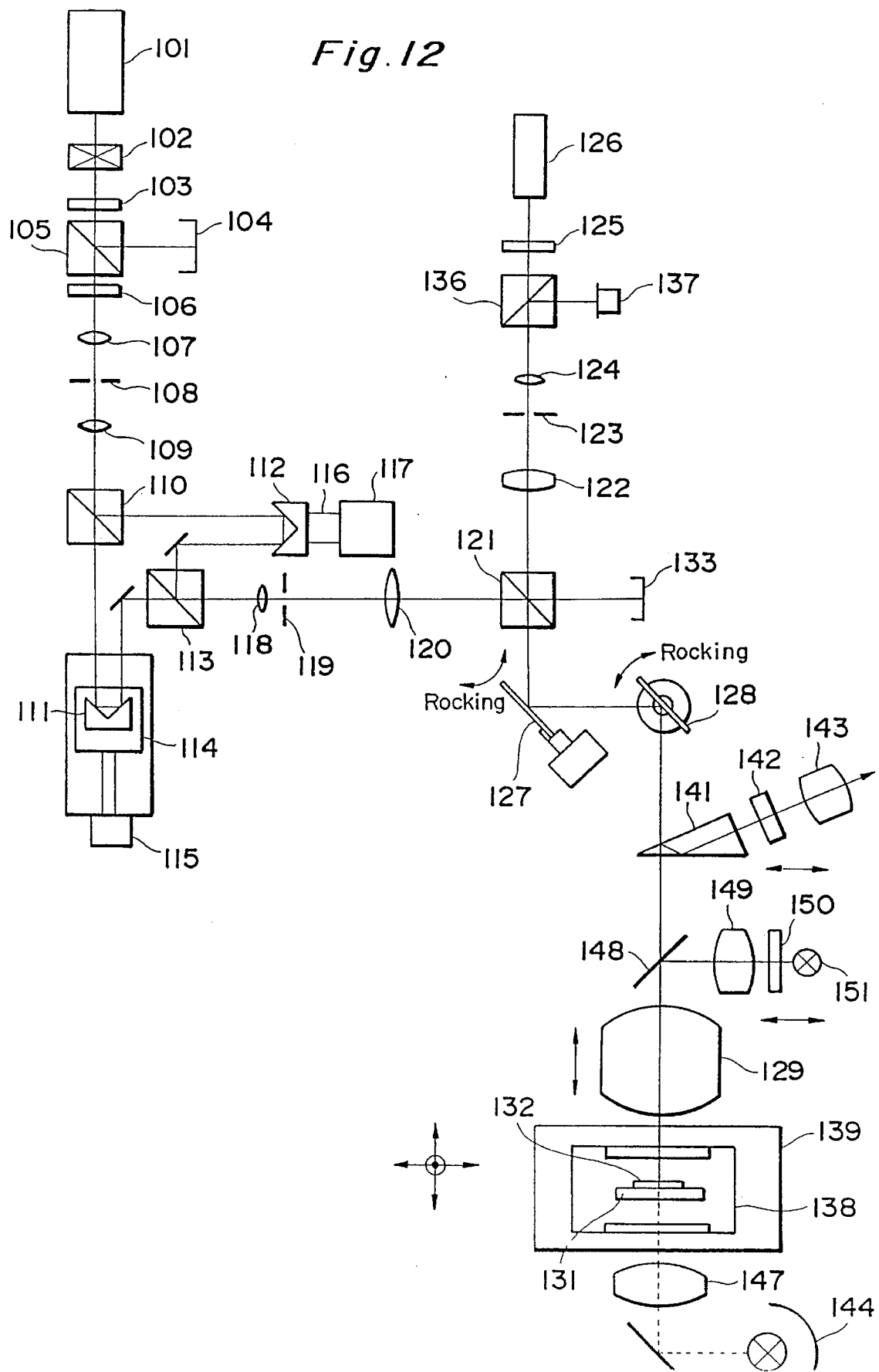

The eleventh embodiment is described referring to FIG. 12. In FIG. 12, the same reference numerals denote the same or equivalent constituent elements as those in FIG. 11. The present embodiment is different from the tenth embodiment in that the space scanning is carried out by a Y scan mirror (galvanomirror) 127 and an X scan mirror (galvanomirror) 128 while a double-side windowed cryostat 138 and a sample table 131 are fixed, whereby realizing the two-dimensional scan. The present embodiment is effective to detect an image of scanning confocal microscope and an optical echo by independent photodetectors as well as to observe an image of ordinary microscope.

Embodiment 12

Figure 13:
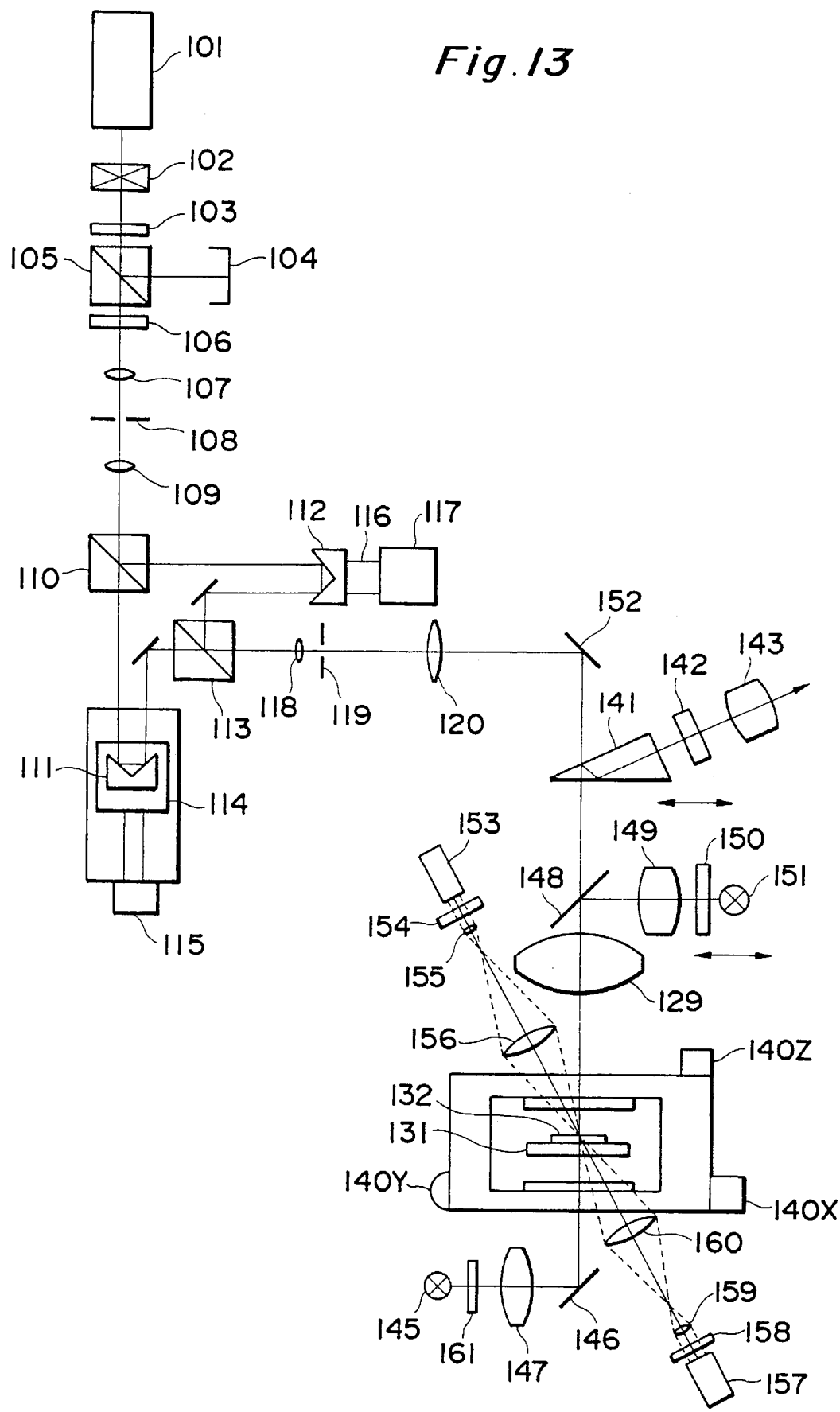

The twelfth embodiment is described referring to FIG. 13. In FIG. 13, the same reference numerals denote the same or equivalent constituent elements as those in FIG. 11. This embodiment is so arranged that a beam traveling from a light splitter 113 through a lens 118, a pin hole 119 and a lens 120 is reflected by a plane mirror 152 to enter an objective lens system 129. Further, the embodiment is arranged to detect scattered light and fluorescence of specimen 132 away from the optical axis of objective lens system 129. In more detail, the apparatus has a first optical system composed of a photodetector 153, a filter 154, and lenses 155, 156, and a second optical system composed of a photodetector 157, a filter 158 and lenses 159, 160. The specimen 132 is illuminated by an illumination mechanism composed of a light source 145, a filter 161, a lens 147 and a mirror 146 or by an illumination mechanism composed of a beam splitter or the like 148, a lens 149, a filter 150 and a light source 151. An observation image of specimen 132 is observed through an eyepiece lens system composed of a prism 141, a filter 142 and a lens 143. After a position for detection of optical echo signal is confirmed, the prism 141 is taken out of the optical system, and the optical echo is detected by the photodetector 153 or 157.

Embodiment 13

Figure 14:
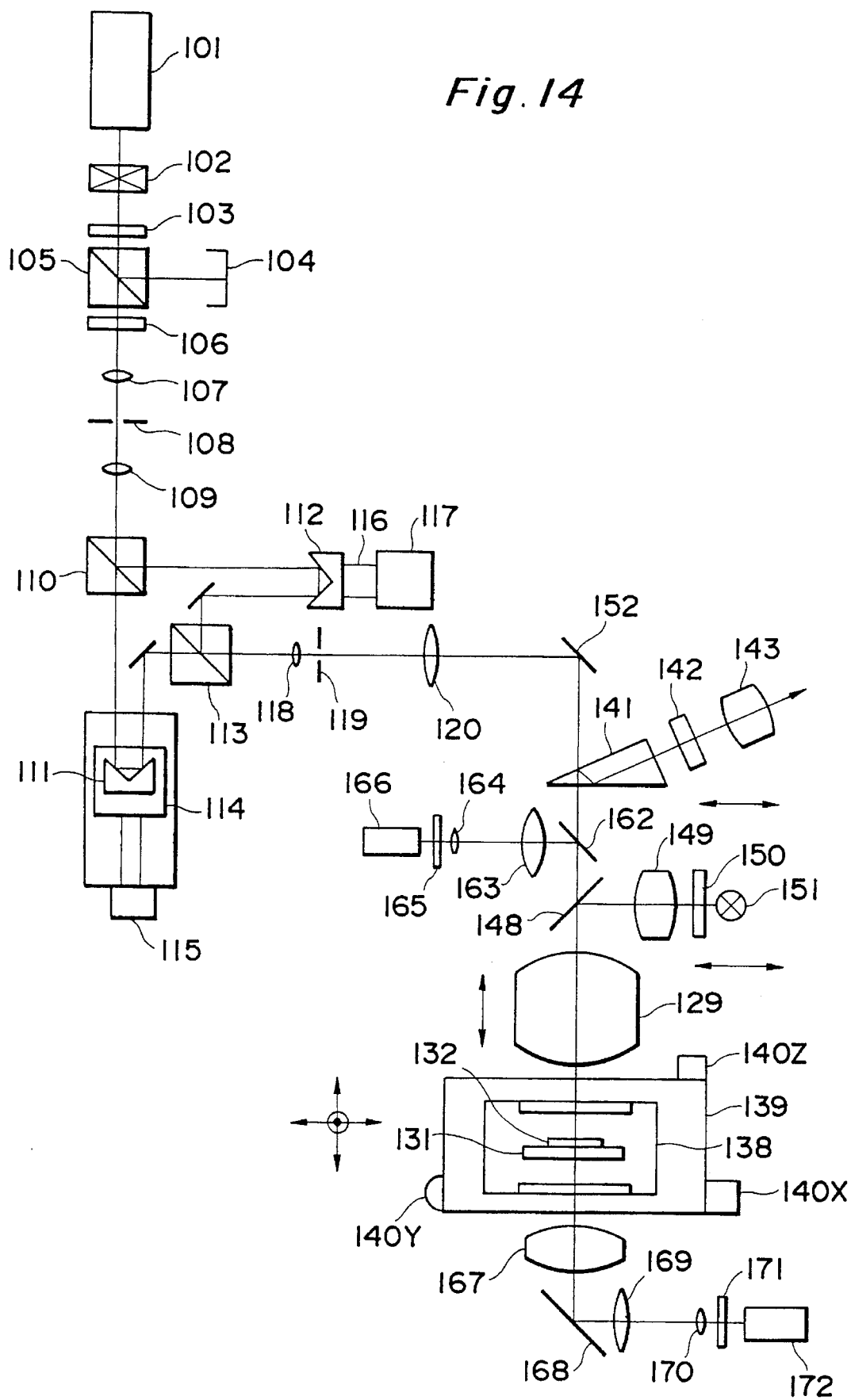

The thirteenth embodiment is described referring to FIG. 14. In FIG. 14, the same reference numerals denote the same or equivalent constituent elements as those in FIG. 13. This embodiment is arranged to detect the optical echo signal without employing the confocal arrangement. For that purpose, there are an optical system, which is composed of a semitransparent mirror (or beam splitter) 162, lenses 163, 164, a filter 165 and a photodetector 166, disposed between a plane mirror 152 and a semitransparent mirror (or beam splitter) 148, and another optical system, which is composed of a lens 167, a mirror 168, lenses 169, 170, a filter 171 and a photodetector 172, disposed behind the specimen 132.

Embodiment 14

Figure 15:
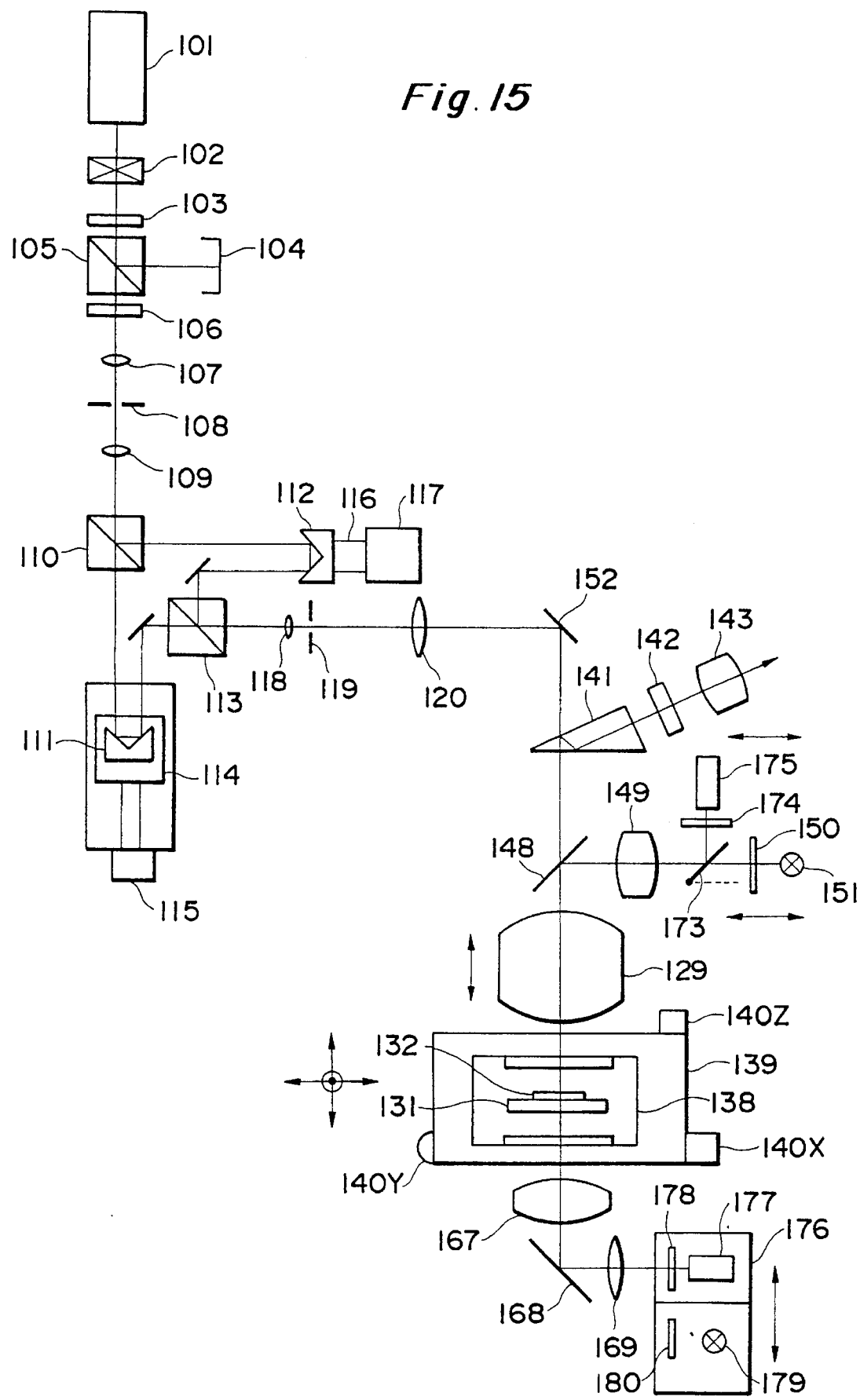

The fourteenth embodiment is described referring to FIG. 15. In FIG. 15, the same reference numerals denote the same or equivalent constituent elements as those in FIG. 14. This embodiment is a modification of the thirteenth embodiment. Specifically, a rockable rotation mirror 173 is provided between a lens 149 and a filter 150 following a semitransparent mirror (or beam splitter) 148, so that the optical path may be changed when the rotation mirror 173 is inserted between the lens 149 and the filter 150. Further, a filter 174 and a photodetector 175 are provided in series along the direction of thus changed optical path. Accordingly, the optical echo can be detected with the rotation mirror 173 inserted between the lens 149 and the filter 150, while a reflection microscope image can be observed through an eyepiece lens system comprised of a prism 141, a filter 142 and a lens 143 with the rotation mirror 173 away from between the lens 149 and the filter 150.

Also, a change-over stage 176 comprises in parallel an optical system composed of a photodetector 177 and a filter 178, and an illumination system composed of a light source 179 and a filter 180. Moving the change-over stage 176 can take the optical system or the illumination system selectively to the position where either one can face a lens 169. Accordingly, a transparent microscope image of specimen 132 can be observed through the eyepiece lens system when the change-over stage 176 is moved to irradiate the back face of specimen 132 with illumination light from the illumination system. On the other hand, the optical echo can be detected when the change-over stage 176 is moved to make the optical system face the lens 169.

Embodiment 15

Figure 16:
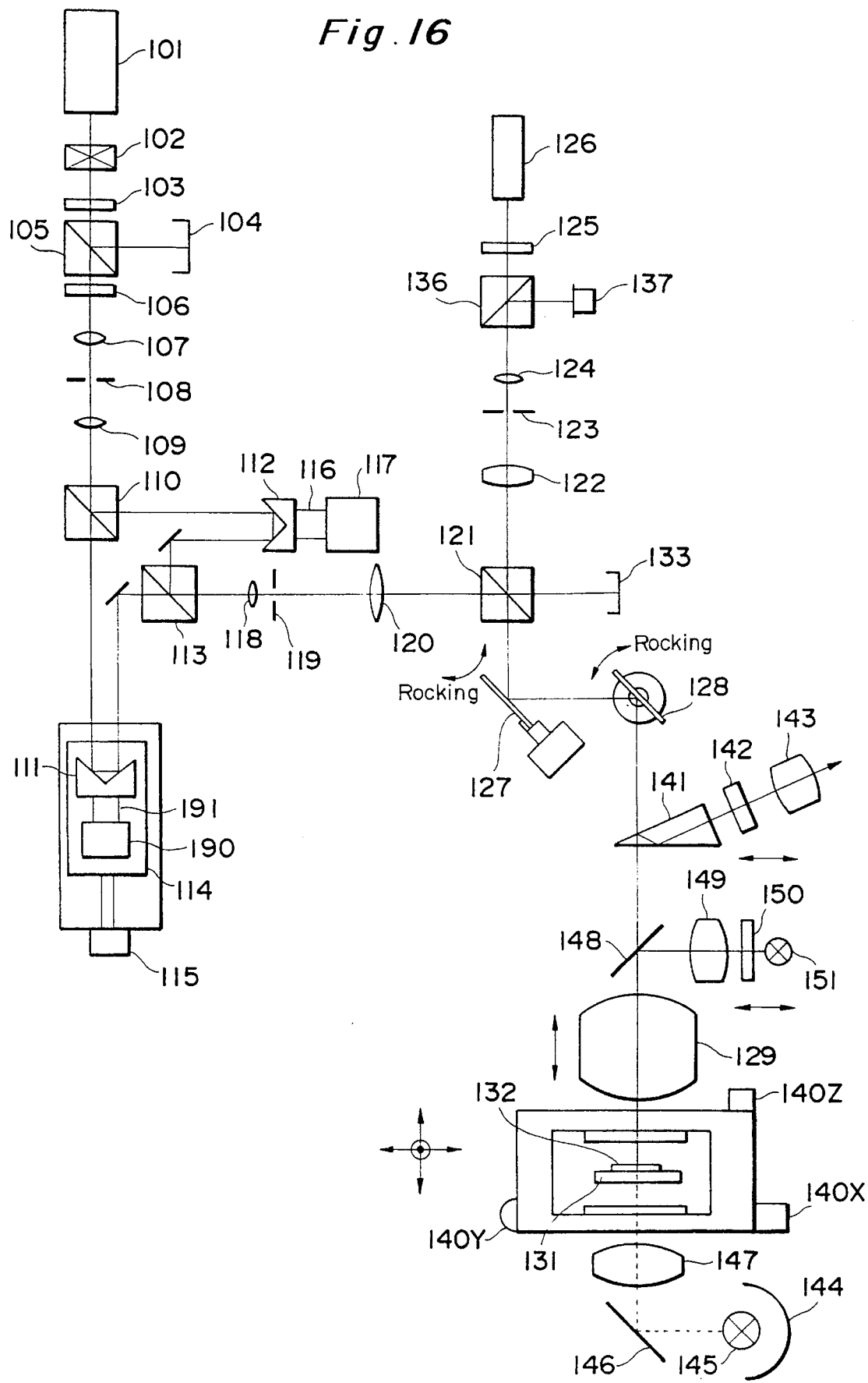

The fifteenth embodiment is described referring to FIG. 16. In FIG. 16, the same reference numerals denote the same or equivalent constituent elements as those in FIG. 12. The present embodiment is a modification to enhance the SN ratio of optical echo signal.

Specifically, a piezoelectric device 191 driven by an AC power source 190 of predetermined frequency is mounted on a sliding stage 114 driven by a displacer 115 comprising a drive motor or an actuator, and a corner cube 111 is attached to the piezoelectric device 191. The piezoelectric device 191 may be driven at a frequency equal to that of piezoelectric device 116 for corner cube 112 or different from it.

If the two piezoelectric devices are driven at the same frequency, the modulation depth will change depending upon a fixed phase difference between the phase modulations effected by the respective piezoelectric devices 116 and 191. The modulation depth becomes maximum when the phase difference is a half of wavelength. The best SN ratio may be readily attained in this case because a deeper phase modulation depth can be obtained at the same AC drive voltage value than that in case of only one of corner cubes 111, 112 being vibrated. In case that the piezoelectric devices 116, 191 are driven at different modulation frequencies, the frequency at which the optical echo signal appears becomes higher than that in case of only one of corner cubes 111, 112 being vibrated, which can also improve the SN ratio of optical echo signal.

Embodiment 16

Figure 17:
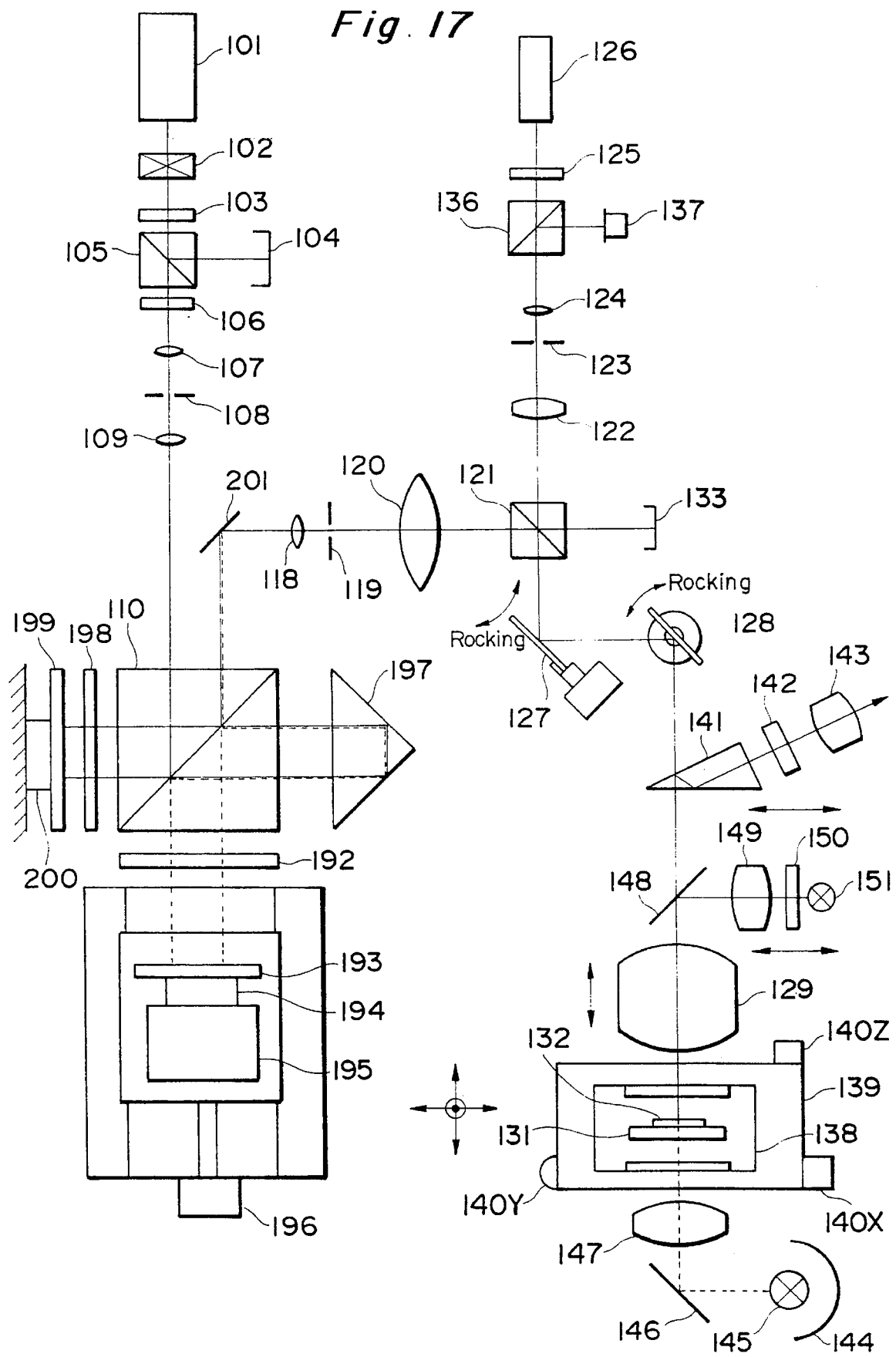

The sixteenth embodiment is described referring to FIG. 17. In FIG. 17, the same reference numerals denote the same or equivalent constituent elements as those in FIG. 16. The present embodiment has the same object as the fifteenth embodiment, and is a modification to enhance the SN ratio of optical echo signal.

The present embodiment obviates the corner cubes provided in the first to fifteenth embodiments, but instead includes a beam splitter 110 and an optical system attached thereto and having the same function as the corner cubes. Specifically, a quarter wave plate 192 and a plane mirror 193 are disposed behind the beam splitter 110 along the incident direction of laser beam from light source 101, and the plane mirror 193 is attached to a piezoelectric device 194 driven by an AC source 195. A right-angle prism (or corner cube prism) 197 is disposed on a side of beam splitter 110, and a quarter wave plate 198 and a plane mirror 199 are disposed in series on another side of beam splitter 110 (on the opposite side to the right-angle prism 197). The plane mirror 199 is attached to a piezoelectric device 200. A plane mirror 201 reflects a beam outgoing from the beam splitter 110 toward a lens 118.

The plane mirror 193 and the right-angle prism (or corner cube prism) 197 constitute a loop optical system in such an arrangement. This arrangement can provide four times deeper modulation depth at the same drive voltage of piezoelectric devices than that of the phase modulation optical system shown in FIG. 8 for example. Even if either one of piezoelectric devices 194, 200 is driven, the SN ratio of optical echo signal can be sufficiently improved.

Embodiment 17

Figure 18:
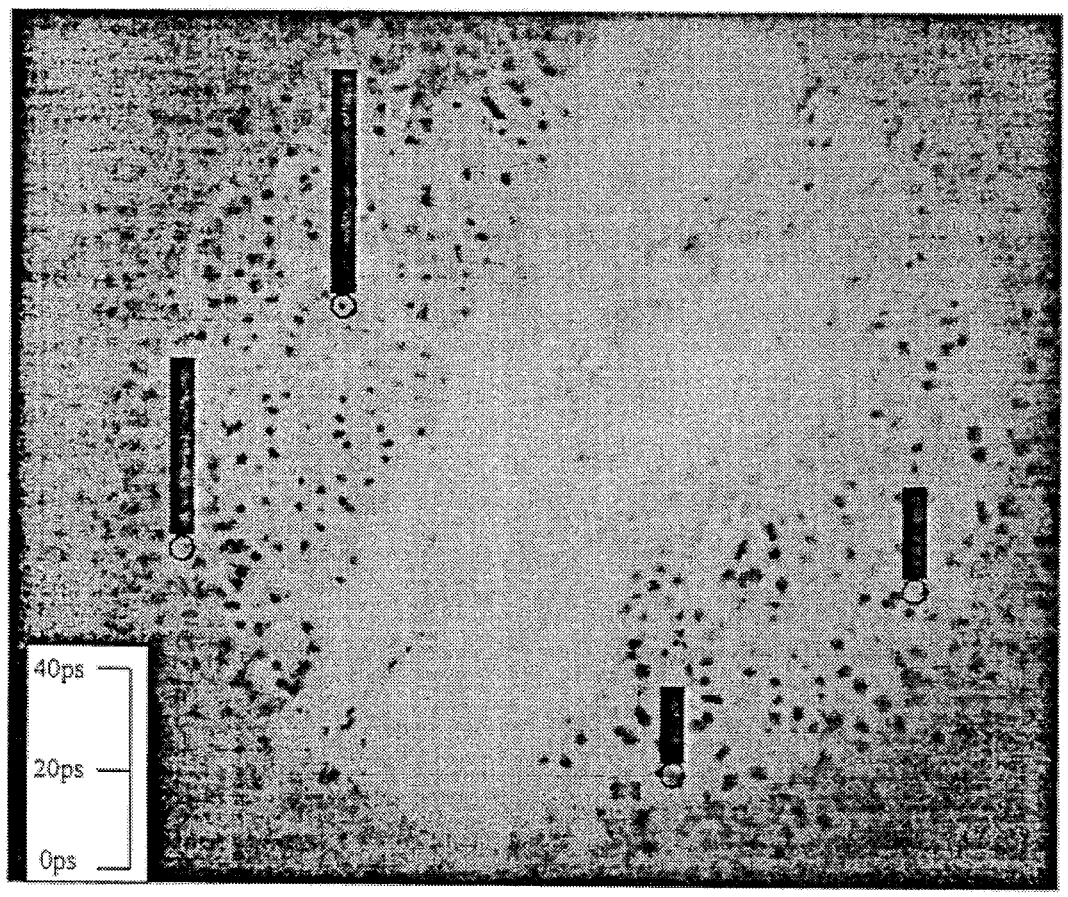
FIG. 18 is a drawing to show a human pancreas stained by Texas Red dye on which phase relaxation times obtained by the apparatus in FIG. 16.

The seventeenth embodiment is next described referring to FIG. 18. This embodiment is an example of application in which the optical measuring apparatus of the present invention for observing the optical echo phenomenon is used to measure the physicochemical properties of human pancreas tissue.

FIG. 18 is a drawing to show a human pancreas tissue stained by Texas Red dye on which phase relaxation times obtained by the apparatus in FIG. 16. FIG. 18 shows a measurement result of 4 points at the object to be measured. Two points of left hand and two points of right hand indicate the measurement result of normal tissue and cancer tissue, respectively. Further, a bar chart indicates a phase relaxation time. These images are measured at mode of laser scanning microscope. A cancer portion is clearly discriminated from a normal portion by a border of 20 pico seconds. The conditions for measurement of this figure are as follows.

Incoherent light was made by a dye laser pumped by mode-locked argon ion laser of 80 MHz. The incoherent light was produced, after the entire wavelength selection element such as the birefringent filter was taken out of the dye laser and after the cavity length in synchronously pumped state was then changed into one to maximize the spectrum range. Instead of the electric field correlation time of laser being monitored from spectrum, the correlation time of pulse may be monitored by an autocollimator utilizing the second harmonic generation, and the cavity length may be changed to minimize the correlation time. Four points in FIG. 18 were measured with incoherent light with center wavelength of about 600 nm, bandwidth of about 400 cm$^{-1}$ and correlation time of about 40 femto seconds, using Rhodamine 6G as a dye for dye laser. This corresponds to the absorption band of Texas Red used for staining the sample, which ranges from 570 nm to 610 nm. Incoherent light having passed through the delay system and the objective system was guided to irradiate a sample 132 cooled at about 6 Kelvin, and fluorescence from the sample was selected by sharp cut filter 25 cutting wavelengths below about 680 nm then to be made incident into photomultiplier tube 126. The piezoelectric device was driven for phase modulation at frequency of 23 kHz by AC voltage of amplitude 3V to which a bias voltage of 3V was applied. The laser beam was focused and fixed at a point on the sample by space scanning apparatus 127, 128, 140X, 140Y, 140Z. Then, successively adjusting the delay system, 46 kHz component of fluorescence was detected by the lockin amplifier and obtained data was stored in the data processing device. The delay unit was stopped for ten seconds for each delay time. A phase relaxation time was calculated based on the data and stored together with position data in the data processing device. Successive scanning was carried out by the space scanning apparatus, and obtained phase relaxation times were mapped.

An image of scanning confocal microscope was synthesized as follows. While the galvanomirrors 127, 128 were controlled to make the focus point of laser beam uniformly scan the entire area over the sample to be observed, DC output from photodiode 137 was stored in the image frame memory.

The result of mapping of phase relaxation time was output to a display (CRT) together with the scanning microscope image. Of course, a hard copy of data can be obtained. Comparing the result with that by another tissue examination method, for example with a result of microscopic visual inspection of shape of cell nuclei, it was found for the sample used in the present embodiment that the region with phase relaxation time of not more than 20 pico seconds substantially corresponded to the portion of abnormal tissue.

There are as sample preparing method a method for preparing a frozen and unfixed sample and a method for preparing a fixed sample with formalin or the like. First described is the method for preparing a frozen and unfixed sample. After a tissue is extirpated from a human body, the tissue is quickly frozen in liquid nitrogen. Then, the tissue is sliced by microtome in thickness of about 4 microns in a freezer at −30 degrees, and the sliced tissue is set on slide glass. This sample is dipped in Texas Red aqueous solution as tissue staining dye for ten minutes for about staining. The staining dye may be Rhodamine 640. After the dye sticking to the surface is washed with distilled water, a mounting agent is applied on the sample and cover glass is placed over it for sealing. This sample is mounted on a sample holder in sample chamber and then cooled therein.

The fixed sample preparation method is next described. After a tissue is extirpated from a human body, it is dipped in formalin solution for about 48 hours to obtain a fixed tissue. After the tissue is washed with water, the tissue is dipped in six tanks of 99.5% methanol solution and a tank of 100% methanol for two hours each to remove water. Further, the tissue is dipped in three tanks of xylene solution for two hours each and in three tanks of fused paraffin for one hour each. Then, an embedding receptacle is filled with fused paraffin and the tissue piece is dipped therein for cooling and solidification. This sample is sliced by microtome in thickness of about 4 microns and the sliced sample is set on slide glass. Paraffin is next removed from the sample in this state. The sample on slide glass is put in and taken out of three tanks of xylene and four tanks of at least 99.5% methanol 20 times each. After the sample is washed with distilled water, it is dipped in Texas Red aqueous solution as tissue staining dye for about ten minutes for staining. The staining dye may be Rhodamine 640. After the dye sticking to the surface is washed with distilled water, a mounting agent is applied over it and cover glass is put on it for sealing. This sample is mounted on a sample holder in sample chamber and cooled therein.

Although the space scanning was done in the example of FIG. 18, the optical echo may be measured for sample evaluation without space scan but with use of the apparatus of FIG. 15 for example. In this case, the focus position of laser is fixed at a point and samples are changed one by one to measure respective phase relaxation times thereof. Whether cancer is present or absent can be judged at that point on each sample by observing whether the phase relaxation time thereof is greater than 20 pico seconds for the case of pancreas tumor. Namely, it can be utilized for screening test of plural samples. Although the echo light was detected from fluorescence from specimen in the example of FIG. 18, transmitted light may also be detected as echo light. The sharp cut filter is unnecessary for such detection.

The temperature was fixed at about 6 Kelvin in the example of FIG. 18, but the sample temperature may be changed. For example, if the sample temperature is taken in into the data processing device and if the same measurement is repeated while successively changing the sample temperature, phase relaxation times may be calculated at respective temperatures and at respective positions. The data processing device executes fitting of change of phase relaxation time with temperature change at each position to the power of temperature T ($T^a$) to calculate exponent a at each position. It is generally known that the phase relaxation time is proportional to the power of temperature T. Mapping the exponent a in accordance with positional information, a map is obtained for temperature dependency of phase relaxation time, whereby a delicate difference of histological condition can be detected. This method may be of course utilized for screening test of plural samples without scanning space but with exchanging samples to compare exponents a thereof.

Although the test was done by directly obtaining the phase relaxation time in the above methods, the test is also possible by the following method. A point is selected in space by the space scanning apparatus, and echo is measured with delay time fixed. The space scanning apparatus successively scans measuring points, and an echo intensity at each point is stored together with position data therefor. If the delay time is constant, the echo intensity is stronger with longer phase relaxation time. This is because a longer delay time hardly weakens the echo if the phase relaxation time is long enough. Accordingly, mapping based on these data may be considered approximately equivalent to mapping with phase relaxation time. Use of this method can reduce the inspection time to permit faster completion of test than the method for calculating the phase relaxation time for each point. In addition to the mapping, this method can be of course used for screening test of plural samples without scanning space but with exchanging samples. There are some samples from which the echo cannot be measured because of very short phase relaxation time. Mapping or screening test will be done for such cases by detecting presence or absence of echo signal.

Although the above examples described the samples of human tissue, the apparatus of the present invention may also be applied to inspection of polymer samples to obtain a distribution state of amorphous part and crystalline part.

What is claimed is:

1. An optical measuring apparatus comprising:

a laser beam source;

a light splitter for splitting light emitted from said laser beam source into two beams transmitting in different directions;

an optical delay unit disposed in an optical path of one of said beams outgoing from said light splitter;

a phase modulator disposed in an optical path of the other of said beams outgoing from said light splitter, for phase-modulating said other beam by a predetermined frequency;

an optical mixer for mixing two beams respectively outgoing from said optical delay unit and from said phase modulator;

an illumination optical system for guiding a mixed beam outgoing from said optical mixer onto a specimen to form a light spot thereon;

a photodetector for detecting light from said specimen; and signal processing means for extracting a modulation component with a frequency even times larger than the modulation frequency of said phase modulator from an output signal from said photodetector and detecting an intensity of optical echo depending upon an optical delay time set by said optical delay unit.

2. An optical measuring apparatus comprising:

a laser beam source;

a light splitter for splitting light emitted from said laser beam source into two beams transmitting in different directions;

an optical delay unit disposed in an optical path of one of said beams outgoing from said light splitter, for producing an optical delay to said beam;

a phase modulator disposed in an optical path of the other of said beams outgoing from said light splitter, for phase-modulating said other beam by a predetermined frequency;

an optical mixer for mixing two beams respectively outgoing from said optical delay unit and from said phase modulator;

an illumination optical system for guiding a mixed beam outgoing from said optical mixer onto a specimen to form a light spot thereon;

scanning means for effecting scanning of said light spot formed on said specimen by said illumination optical system relative to said specimen;

a photodetector for detecting light from said specimen; and signal processing means for extracting a modulation component with a frequency even times larger than the modulation frequency of said phase modulator from an output signal from said photodetector and detecting an intensity of optical echo depending upon an optical delay time set by said optical delay unit.

3. An optical measuring apparatus comprising:

a laser beam source;

a light splitter for splitting light emitted from said laser beam source into two beams transmitting in different directions;

an optical delay unit disposed in an optical path of one of said beams outgoing from said light splitter, for producing an optical delay to said beam;

a phase modulator disposed in an optical path of the other of said beams outgoing from said light splitter, for phase-modulating said other beam by a predetermined frequency;

an optical mixer for mixing two beams respectively outgoing from said optical delay unit and from said phase modulator;

an optical system for guiding a mixed beam outgoing from said optical mixer into an optical microscope and thereby forming a light spot of said mixed beam on a specimen through said optical microscope;

a photodetector for detecting light from said specimen through said optical microscope; and signaling processing means for extracting a modulation component with a frequency even times larger than the modulation frequency of said phase modulator from an output signal from said photodetector and detecting an intensity of optical echo depending upon an optical delay time set by said optical delay unit.

4. An optical measuring apparatus comprising:

a laser beam source;

a light splitter for splitting light emitted from said laser beam source into two beams transmitting in different directions;

an optical delay unit for changing an optical path of one of said beams outgoing from said light splitter and a phase modulator for phase-modulating said one of beams by a predetermined frequency;

an optical mixer for mixing said beam phase-modulated having said optical path changed and the other of said beams outgoing from said light splitter;

an illumination optical system for guiding a mixed beam outgoing from said optical mixer onto a specimen to form a light spot thereon;

a photodetector for detecting light from said specimen; and signal processing means for extracting a modulation component with a frequency even times larger than the modulation frequency of said phase modulator from an output signal from said photodetector and detecting an intensity of optical echo depending upon an optical delay time set by said optical delay unit.

5. An optical measuring apparatus comprising:

a laser beam source;

a light splitter for splitting light emitted from said laser beam source into two beams transmitting in different directions;

an optical delay unit for changing an optical path of one of said beams outgoing from said light splitter and a phase modulator for phase-modulating said one of beams by a predetermined frequency;

an optical mixer for mixing said beam phase-modulated having said optical path changed and the other of said beams outgoing from said light splitter;

an illumination optical system for guiding a mixed beam outgoing from said optical mixer onto a specimen to form a light spot thereon;

scanning means for effecting scanning of said light spot formed on said specimen by said illumination optical system relative to said specimen;

a photodetector for detecting light from said specimen; and signal processing means for extracting a modulation component with a frequency even times larger than the modulation frequency of said phase modulator from an output signal from said photodetector and detecting an intensity of optical echo depending upon an optical delay time set by said optical delay unit.

6. An optical measuring apparatus comprising:

a laser beam source;

a light splitter for splitting light emitted from said laser beam source into two beams transmitting in different directions;

an optical delay unit for changing an optical path of one of said beams outgoing from said light splitter and a phase modulator for phase-modulating said one of beams by a predetermined frequency;

an optical mixer for mixing said beam phase-modulated having said optical path changed and the other of said beams outgoing from said light splitter;

an optical system for guiding a mixed beam outgoing from said optical mixer into an optical microscope and thereby forming a light spot of said mixed beam on a specimen through said optical microscope;

a photodetector for detecting light coming from said specimen through said optical microscope; and signal processing means for extracting a modulation component with a frequency even times larger than the modulation frequency of said phase modulator from an output signal from said photodetector and detecting an intensity of optical echo depending upon an optical delay time set by said optical delay unit.

7. An optical measuring apparatus according to either one of claim 1 to claim 6, wherein said laser beam source has a time coherence shorter than an optical phase relaxation time of a light absorption band of specimen to be watched.

8. An optical measuring apparatus according to either one of claim 1 to claim 6, wherein said laser beam source emits light having a center wavelength on a longer wavelength side than a wavelength having a maximum absorption coefficient out of wavelengths in a light absorption band of said specimen.

9. An optical measuring apparatus according to either one of claim 1 to claim 6, wherein said laser beam source emits light having a center wavelength adjusted as longer than a wavelength having a maximum absorption coefficient out of wavelengths in a light absorption band of said specimen.

10. An optical measuring apparatus according to either one of claim 1 to claim 6, further comprising:

a light source for emitting light with a wider spectrum than that of said light from said laser beam source in a same optical path as an optical path of said light emitted from said laser beam source; and means for obtaining a wavelength having a maximum absorption coefficient out of wavelengths in a light absorption band of said specimen, using the light from said light source.

11. An optical measuring apparatus according to either one of claim 1 to claim 6, further comprising a light source for irradiating said specimen with another light to reduce influence of light caused in said specimen after said specimen was irradiated with the light spot from said illumination optical system.

12. An optical measuring apparatus according to either one of claim 1 to claim 6, further comprising a light source for irradiating said specimen with another light to reduce influence of light caused in said specimen before said specimen is irradiated with the light spot from said illumination optical system.

13. An optical measuring apparatus according to claim 2 or claim 5, wherein a relative scanning speed of said light spot on said specimen by said scanning means is sufficiently slower than the phase modulation by said phase modulator.

14. An optical measuring apparatus according to either one of claim 1 to claim 6, wherein said photodetector comprises a shield member having a pin hole aperture for receiving the light from said specimen and wherein said pin hole aperture of said shield member is conjugate with a focus spot in/on said specimen.

15. An optical measuring apparatus according to claim 2 or claim 5, further comprising a recording device for recording an output signal from said signal processing means in correspondence with a position of the light spot from the illumination optical system by said scanning means and a delay time by said optical delay unit, and for reproducing the output signal with necessity.

16. An optical measuring apparatus according to either one of claim 1 to claim 6, further comprising a data analyzing device for analyzing a change amount of output signal from said signal processing means with a change of delay time of said optical delay unit for a spot irradiating position by said irradiation optical system.

* * * * *